United States Patent
Bachlava et al.

(10) Patent No.: US 9,580,724 B2
(45) Date of Patent: Feb. 28, 2017

(54) METHODS AND COMPOSITIONS FOR PRODUCING PLANTS WITH ELEVATED BRIX

(71) Applicant: SEMINIS VEGETABLE SEEDS, INC., St. Louis, MO (US)

(72) Inventors: Eleni Bachlava, Vallejo, CA (US); Joseph J. King, Davis, CA (US); Subash Krishnamurthy, St. Peters, MO (US); Jeffrey M. Mills, Woodland, CA (US); Adam M. Wentzell, Davis, CA (US)

(73) Assignee: Seminis Vegetable Seeds, Inc., Woodland, CA (US)

( * ) Notice: Subject to any disclaimer, the term of this patent is extended or adjusted under 35 U.S.C. 154(b) by 805 days.

(21) Appl. No.: 13/875,220

(22) Filed: May 1, 2013

(65) Prior Publication Data

US 2013/0298278 A1 Nov. 7, 2013

Related U.S. Application Data

(60) Provisional application No. 61/642,978, filed on May 4, 2012.

(51) Int. Cl.
| | |
|---|---|
| *C12N 15/82* | (2006.01) |
| *A01H 5/06* | (2006.01) |
| *C12Q 1/68* | (2006.01) |
| *A01H 5/08* | (2006.01) |

(52) U.S. Cl.
CPC ............. *C12N 15/825* (2013.01); *A01H 5/08* (2013.01); *C12N 15/8245* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | |
|---|---|---|
| 8,053,631 B2 | 11/2011 | Broglie et al. |
| 2003/0135886 A1 | 7/2003 | Zamir et al. |
| 2006/0005284 A1 | 1/2006 | Tolla et al. |
| 2007/0039076 A1 | 2/2007 | Boukharov et al. |
| 2009/0007291 A1 | 1/2009 | Knerr |
| 2009/0031438 A1 | 1/2009 | Kennard et al. |
| 2011/0283402 A1 | 11/2011 | Bunn et al. |
| 2013/0055466 A1 | 2/2013 | Juarez et al. |

OTHER PUBLICATIONS

Monforte et al. (Theor. Appl. Genet. (2004) 108: pp. 750-758).*
European Extended Search Report for Application No. EP13784196, dated Nov. 3, 2015.
Paris et al., "Genetic dissection of fruit quality components in melon (*Cucumis melo* L.) using a RIL population derived from exotic x elite US Western Shipping germplasm," *Mol. Breeding* 22:405-419, 2008.
Diaz et al., "A consensus linkage map for molecular markers and Quantitative Trait Loci associated with economically important traits in melon (*Cucumis melo* L.)," *BMC Plant Biology* 11:111, 2011.
Obando-Ulloa et al., "Identification of QTLs related to sugar and organic acid composition in melon using near-isogenic lines," *Scientia horticulturae* 121:425-433, 2009.
Monforte et al., "Identification of quantitative trait loci involved in fruit quality traits in melon (*Cucumis melo* L.)," *Theor. Appl. Genet.* 108:750-758, 2004.
U.S. Appl. No. 13/960,545, filed Aug. 6, 2013, Bachlava et al.
Bernacchi et al., "Advanced backcross QTL analysis of tomato. I. Identification of QTL for traits of agronomic importance from *Lycopersicon hirsutum*," *Theor. Appl. Genet.* 97:381-397, 1998.
Hawkins et at, "Linkage mapping in a watermelon population segregating for *Fusarium* wilt resistance," *J. Am. Soc. Horticultural Sci.* 126(3):344-350, 2001.
Sandlin, "Genetic Mapping in Citrullus Lanatus," *A Masters Thesis Submitted to the Graduate Faculty of the University of Georgia*, 2010.
Tanksley et al., "Advanced backcross QTL analysis: a method for the simultaneous discovery and transfer of valuable QTLs from unadapted germplasm into elite breeding lines," *Theor. Appl. Genet.* 92:191-203, 1996.
Wang et al., Windows QTL Cartographer 2.5. Department of Statistics, North Carolina State University, Raleigh, NC. (http://statgen.ncsu.edu/qtlcart/WQTLCart.htm), 2012.

* cited by examiner

*Primary Examiner* — Brent Page
*Assistant Examiner* — Jared Shapiro
(74) *Attorney, Agent, or Firm* — Dentons US LLP; Matthew L. Madsen Esq.

(57) ABSTRACT

The invention provides compositions and methods relating to the production of *Cucumis melo* plants with elevated Brix and/or enhanced fruit color. The invention further provides plants, plant parts, and seeds comprising such elevated Brix. The invention allows introgression of the identified high Brix QTL in an desired genetic background of a sexually compatible plant species.

17 Claims, 7 Drawing Sheets

SEQUENCE LISTING

<160> NUMBER OF SEQ ID NOS: 110

<210> SEQ ID NO 1
<211> LENGTH: 121
<212> TYPE: DNA
<213> ORGANISM: Cucumis melo

<400> SEQUENCE: 1
cgagtcaagg caagctggag gacgcactgt atcgcagtca tgctcgacag gacatgttgc      60
mtgtggccgc atgatcgctc cgacaccttt tactattttc tttcatcgta ttttagtttc     120
t                                                                      121

<210> SEQ ID NO 2
<211> LENGTH: 121
<212> TYPE: DNA
<213> ORGANISM: Cucumis melo

<400> SEQUENCE: 2
tgttggattt aagaagactt taaatgctat catctcacag ctacctaagc acagacaaac      60
stttctgttc tcagcaactc aaacgaagtc tgttcaggat cttgccagac tcagtttgaa     120
a                                                                      121

<210> SEQ ID NO 3
<211> LENGTH: 121
<212> TYPE: DNA
<213> ORGANISM: Cucumis melo

<400> SEQUENCE: 3
ttggtcgttt tggtgtgtcg gtattcaagt tgattagttt gtttgtagct tttaagttcg      60
yaactgtttg gtaggagctc tgatagaatt ttacttgctg tttatatact tctgtttccc     120
t                                                                      121

<210> SEQ ID NO 4
<211> LENGTH: 121
<212> TYPE: DNA
<213> ORGANISM: Cucumis melo

<400> SEQUENCE: 4
ctctcacagt ggcgcagcct ttcgcctcct cgaatctgtc acattttag ggcggacatg       60 rtaggtgtta tctttggctg ttgggaaata taaagtgaaa taaaacatttt gtgtgtggtg    120 a                                                                      121

<210> SEQ ID NO 5
<211> LENGTH: 121
<212> TYPE: DNA
<213> ORGANISM: Cucumis melo

<400> SEQUENCE: 5
ccaaataagc ctggaagatg actcagtata ttcttcacca ttttaactac gaaatctttt      60
sgattcctgg acattttcat ttcgcttgct tttgattctt cctcctggat aacattttct    120
t                                                                      121

<210> SEQ ID NO 6
<211> LENGTH: 121
<212> TYPE: DNA
<213> ORGANISM: Cucumis melo
<220> FEATURE:
<221> NAME/KEY: misc_feature

```
<222> LOCATION: (118)..(118)
<223> OTHER INFORMATION: n is a, c, g, or t

<400> SEQUENCE: 6
cacccatgct gatgcactac gcctggcact agaaatgagt ccatacgaga gagaaaatcc    60
rtccaagact gcaggaagag ggacaacccc aggtcagaag aggaaggctg agttgcancc   120
t                                                                  121

<210> SEQ ID NO 7
<211> LENGTH: 121
<212> TYPE: DNA
<213> ORGANISM: Cucumis melo

<400> SEQUENCE: 7
tgaaaagaag aagattccat cgaatattcc atctgttccc attgatgaag ttttgtttca    60
yctcgaagaa agcatgcaaa gataaaaata tgtagtgcaa aggcatattg cagatgaggt   120
g                                                                  121

<210> SEQ ID NO 8
<211> LENGTH: 121
<212> TYPE: DNA
<213> ORGANISM: Cucumis melo
<220> FEATURE:
<221> NAME/KEY: misc_feature
<222> LOCATION: (100)..(100)
<223> OTHER INFORMATION: n is a, c, g, or t

<400> SEQUENCE: 8
acttgattct tagttcctct tacaacatca actcttcatt caacgtgtta tgtatataca    60
yagttctaac ccttctctat tttcactctc ttattgaaan ttttttcttt ggctttgttg   120
a                                                                  121

<210> SEQ ID NO 9
<211> LENGTH: 121
<212> TYPE: DNA
<213> ORGANISM: Cucumis melo
<220> FEATURE:
<221> NAME/KEY: misc_feature
<222> LOCATION: (4)..(4)
<223> OTHER INFORMATION: n is a, c, g, or t

<400> SEQUENCE: 9
tggnaatcct tataactaaa agcaaaagaa agacctttgt cttgcaattc tcttaagtca    60
ycaacctttg gttggttcca tgctaaattt tgtatggctt tgttttcttc agcatcccct   120
c                                                                  121

<210> SEQ ID NO 10
<211> LENGTH: 121
<212> TYPE: DNA
<213> ORGANISM: Cucumis melo
<220> FEATURE:
<221> NAME/KEY: misc_feature
<222> LOCATION: (7)..(32)
<223> OTHER INFORMATION: n is a, c, g, or t

<400> SEQUENCE: 10
gacgggnnnn nnnnnnnnnn nnnnnnnnnn nnatcattga tcgagggtat tgcaatttgt    60
yagttactgt ggaactatgg aatccttatc gtttgtgaag tttggttgag tttgtatgct   120
t                                                                  121
```

<210> SEQ ID NO 11
<211> LENGTH: 103
<212> TYPE: DNA
<213> ORGANISM: Cucumis melo

<400> SEQUENCE: 11
atctcttctc tctctcctct tgctctctct ttcaccctct tatgttcttg ctgattccca    60
ytttgaagga tttgaaccag aactcgacga cctcgaagat gac                      103

<210> SEQ ID NO 12
<211> LENGTH: 99
<212> TYPE: DNA
<213> ORGANISM: Cucumis melo

<400> SEQUENCE: 12
atcggaatac acaactcaag attctctctc cctcctcgyg catgaaccaa gatgaaacca    60
tctgtattct tttcttctct tcatcttctc tccaccttc                           99

<210> SEQ ID NO 13
<211> LENGTH: 121
<212> TYPE: DNA
<213> ORGANISM: Cucumis melo

<400> SEQUENCE: 13
aaaaaagaga ttgaagtgca cgattgtata cagagatgca cttacatcaa tattgagtga    60
rgttaaccat tgccttggta ggtgccgggt tagatgttcg tccacaatgg caaggcgagg    120
g                                                                    121

<210> SEQ ID NO 14
<211> LENGTH: 107
<212> TYPE: DNA
<213> ORGANISM: Cucumis melo
<220> FEATURE:
<221> NAME/KEY: misc_feature
<222> LOCATION: (93)..(96)
<223> OTHER INFORMATION: n is a, c, g, or t
<220> FEATURE:
<221> NAME/KEY: misc_feature
<222> LOCATION: (98)..(101)
<223> OTHER INFORMATION: n is a, c, g, or t
<220> FEATURE:
<221> NAME/KEY: misc_feature
<222> LOCATION: (103)..(104)
<223> OTHER INFORMATION: n is a, c, g, or t

<400> SEQUENCE: 14
ccacaaccct ttaccccat gaaaaatttt cctactctcc aatcacwttt gcaatagcat     60
caagcaaaag acaaataaca attacatccc aannnncnnn nannacc                  107

<210> SEQ ID NO 15
<211> LENGTH: 121
<212> TYPE: DNA
<213> ORGANISM: Cucumis melo

<400> SEQUENCE: 15
aaacctattc gccttcttct tcctcaagaa aatcctaaag aaaccctaac cctaaaaacc    60
sttgcaccgc tgctgctgtc actcgcctcc gtcctacatc gctattttc tttcgtaagc    120 c                                                                    121

<210> SEQ ID NO 16
<211> LENGTH: 121

```
<212> TYPE: DNA
<213> ORGANISM: Cucumis melo
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (121)..(121)
<223> OTHER INFORMATION: n is a, c, g, or t

<400> SEQUENCE: 16
tctaaaaagt ggcaaacata tgtccttgtc aaacagcacc gaagtgctcc aacaaagaaa      60
wttggctatg ttcaagtact tcttctattc gcccccaaat aactntgaac gacaatgacc     120 n                                                                    121

<210> SEQ ID NO 17
<211> LENGTH: 121
<212> TYPE: DNA
<213> ORGANISM: Cucumis melo

<400> SEQUENCE: 17
gaagggatca acatcagccc agttttcaac attgcagacc tcaaaaggta caatgcgcct      60
ratggattcc agcttacaat agcagacgca acttgaggac aagtttgatg ctcaggggat     120
g                                                                    121

<210> SEQ ID NO 18
<211> LENGTH: 121
<212> TYPE: DNA
<213> ORGANISM: Cucumis melo

<400> SEQUENCE: 18
ttgagattat taggagaaac tagatctact gtctttgaaa attgtctcat ttttccattg      60
ygggttttgg ccagtctaat aacttttagt tgatcatttc tctttactct gtgcttcatt     120
g                                                                    121

<210> SEQ ID NO 19
<211> LENGTH: 121
<212> TYPE: DNA
<213> ORGANISM: Cucumis melo

<400> SEQUENCE: 19
ttaagtacct aatagattag tacctaagaa ggtgtgatac tattttttggg tctttggtgc     60 wagtgagaat gcacaggaga tggcttgttg ttggtgctgc cacggtgaaa ttgcaaatag     120
a                                                                    121

<210> SEQ ID NO 20
<211> LENGTH: 121
<212> TYPE: DNA
<213> ORGANISM: Cucumis melo

<400> SEQUENCE: 20
gcatctgttt tcatagaatc tgagcagaag cctctctgtt gtctgcattt ggattctcag      60
yaactttgtt ctcaactctt ctgaaaacaa gttttgctg agggagttgg ccgttagaga     120
c                                                                    121

<210> SEQ ID NO 21
<211> LENGTH: 121
<212> TYPE: DNA
```

<213> ORGANISM: Cucumis melo

<400> SEQUENCE: 21
ttatagcaag attaaccaaa ctacacgatg aaccatctgt tctaagtact tgaaccctct   60
ytatcctaag atctttctca gggcctaaat cactcactaa aatattgtct atcctcttca  120
c                                                                 121

<210> SEQ ID NO 22
<211> LENGTH: 121
<212> TYPE: DNA
<213> ORGANISM: Cucumis melo

<400> SEQUENCE: 22
acgcatgcgc tcatatatgt aatccttata cgtggtggat ggtcagcctt tggtgagaac   60
rcctatatgt ttaaaaccat cttgcatatg gatgaacatc ttgtttctat gagttattgt  120
t                                                                 121

<210> SEQ ID NO 23
<211> LENGTH: 121
<212> TYPE: DNA
<213> ORGANISM: Cucumis melo
<220> FEATURE:
<221> NAME/KEY: misc_feature
<222> LOCATION: (113)..(113)
<223> OTHER INFORMATION: n is a, c, g, or t

<400> SEQUENCE: 23
acatggaggg ttgaatgtga attcatcgtc ctcttcacca atagaactat attctgatcc   60
wggaagtcct gaaaataatc attcttctat ctccagtcct ccaaaggttg ggnaatgtcc  120
a                                                                 121

<210> SEQ ID NO 24
<211> LENGTH: 121
<212> TYPE: DNA
<213> ORGANISM: Cucumis melo
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (94)..(94)
<223> OTHER INFORMATION: n is a, c, g, or t

<400> SEQUENCE: 24
actagatatn tagtaatatt tcagttaagg ggtataaggg taattggata acataggaag   60
ytactagtag ttattgtgtt agtgtgatta ctanggtgat tacaacctgt tataaataga  120
g                                                                 121

<210> SEQ ID NO 25
<211> LENGTH: 121
<212> TYPE: DNA
<213> ORGANISM: Cucumis melo

<400> SEQUENCE: 25
tgtggccata tatctcgggt cctgcttgtt ccagcctaat cgaaccaagg gagtgtcagg   60
ytcggagctc tcgtagataa tagtagagtg ctccttatcg cgcaaatcga agacccggac  120
a                                                                 121

<210> SEQ ID NO 26
<211> LENGTH: 121
<212> TYPE: DNA
<213> ORGANISM: Cucumis melo

<400> SEQUENCE: 26

```
ttcactcgtc ggaggaacac tagaggtatg atcaaggaat ttctcctcaa cccatctaat    60
rggaagaagg gtcattttct attatgactc attgaggtgt gggcgatctt ctgaaccttg   120
t                                                                   121
```

<210> SEQ ID NO 27
<211> LENGTH: 121
<212> TYPE: DNA
<213> ORGANISM: Cucumis melo

<400> SEQUENCE: 27

```
accttcggga agaggcagat gagagtttca tttaatgatg cattgataga accataagag    60
yagaagtcaa taatcatgtt cttaatgtct tgcttgagag aaggctagaa aaattttaaa   120
a                                                                   121
```

<210> SEQ ID NO 28
<211> LENGTH: 121
<212> TYPE: DNA
<213> ORGANISM: Cucumis melo
<220> FEATURE:
<221> NAME/KEY: misc_feature
<222> LOCATION: (106)..(106)
<223> OTHER INFORMATION: n is a, c, g, or t

<400> SEQUENCE: 28

```
gttgtggctt tggaagtgtg ctttgacggt gaaggaaggc ttgtctcacc agctaccta     60
raggttgttt ccttcctctt ttagagcggg tcatcactgc cttctncaag gcttcttttc   120
t                                                                   121
```

<210> SEQ ID NO 29
<211> LENGTH: 101
<212> TYPE: DNA
<213> ORGANISM: Cucumis melo

<400> SEQUENCE: 29

```
ctgatacaaa aaagcttgaa tgaagtaaaa tggcaatata ygttattcaa cttgaaatca    60
agagctaaat gtagatgtcg agggagatat caatgacttg a                      101
```

<210> SEQ ID NO 30
<211> LENGTH: 121
<212> TYPE: DNA
<213> ORGANISM: Cucumis melo
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (114)..(114)
<223> OTHER INFORMATION: n is a, c, g, or t

<400> SEQUENCE: 30

```
tagaaccagg atcggtatca aataggctcg acgggattga ccttctttag tagacctata    60
ygacctacag gtgttcaggt tggnagtggg ctgtggcact aaaatcgact gagnaatttg   120
t                                                                   121
```

```
<210> SEQ ID NO 31
<211> LENGTH: 121
<212> TYPE: DNA
<213> ORGANISM: Cucumis melo

<400> SEQUENCE: 31
tgagttcgtc aatttgcatt tgatgattgc ttgcgttgtc aactttaagc tctaactctt      60
rcaactgttt tttactctac aaatgtgttt cttataagtt gctttggcat tgaattacat     120
c                                                                     121

<210> SEQ ID NO 32
<211> LENGTH: 121
<212> TYPE: DNA
<213> ORGANISM: Cucumis melo
<220> FEATURE:
<221> NAME/KEY: misc_feature
<222> LOCATION: (96)..(96)
<223> OTHER INFORMATION: n is a, c, g, or t

<400> SEQUENCE: 32 tttattctttt tttgctcttc acaagcaaga ttaggaaatc tattgtagga tgtaggactc     60
raaggtaaat atataacaca ataaatctca ggtagnaaaa tttgccgaat attggaagaa    120
g                                                                    121

<210> SEQ ID NO 33
<211> LENGTH: 121
<212> TYPE: DNA
<213> ORGANISM: Cucumis melo
<220> FEATURE:
<221> NAME/KEY: misc_feature
<222> LOCATION: (23)..(23)
<223> OTHER INFORMATION: n is a, c, g, or t

<400> SEQUENCE: 33
ttgcttttcg acctgaaaac ttngatatga tcactaccaa gaacaccaaa ccggaaatca     60
yccacagagc aataatccac gacctcaaag aactaaagat cccatcctct tttgcctcca    120
c                                                                    121

<210> SEQ ID NO 34
<211> LENGTH: 121
<212> TYPE: DNA
<213> ORGANISM: Cucumis melo

<400> SEQUENCE: 34
ctttcttttg ccttctctta gtactggaga cgagaaagta atcagtggtc ttgcatgctt     60
rttctcagaa gttgggcaag cagtatgttg ctgtggactc ctgtttgtgt tataattatt    120
a                                                                    121

<210> SEQ ID NO 35
<211> LENGTH: 121
<212> TYPE: DNA
<213> ORGANISM: Cucumis melo

<400> SEQUENCE: 35
ctgcaggctt ccacatcttc aatgtaaaaa tgccttcctc tgtccaatgc aatagtgcaa     60
ytggcttact tttcagctaa ctacctccac ttttgttttg aagctcgccg gaggagactg    120
g                                                                    121
```

```
<210> SEQ ID NO 36
<211> LENGTH: 98
<212> TYPE: DNA
<213> ORGANISM: Cucumis melo
<220> FEATURE:
<221> NAME/KEY: misc_feature
<222> LOCATION: (6)..(6)
<223> OTHER INFORMATION: n is a, c, g, or t

<400> SEQUENCE: 36
acatantccc ccttctctcg cacaaacatt aaatgcacgt caaccaacat cacgccaccc     60
rtcgactctc cctccaccag ctttgctggc agcaggac                             98

<210> SEQ ID NO 37
<211> LENGTH: 121
<212> TYPE: DNA
<213> ORGANISM: Cucumis melo

<400> SEQUENCE: 37
ttgtaaggtc caaagagttt tggagataat ttttcattcc ttttctttct caaggatgtc     60
wgatggtaca acctaattgc tttttttctca ttctcctgtt caatcacttt catctatgtt   120
t                                                                    121

<210> SEQ ID NO 38
<211> LENGTH: 121
<212> TYPE: DNA
<213> ORGANISM: Cucumis melo
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t

<400> SEQUENCE: 38
ttgacagcag tatttccaac gtcaatgagt nggtctgacg gctaaatggt acttcggctt     60
rgctgaacgt ctcttttctt ctctccngtg ctgatgagtg ttcatgattg atttgcagaa   120
g                                                                    121

<210> SEQ ID NO 39
<211> LENGTH: 121
<212> TYPE: DNA
<213> ORGANISM: Cucumis melo

<400> SEQUENCE: 39
gcttcagttt ctccttgaat ataccaaaca tgctgtgggc cttcatactt gattatatcg     60
wagtgcaaga tttcatcctt actttattgc tttttgaact gtatgctttc tgtggggata   120
t                                                                    121

<210> SEQ ID NO 40
<211> LENGTH: 121
<212> TYPE: DNA
<213> ORGANISM: Cucumis melo
<220> FEATURE:
<221> NAME/KEY: misc_feature
<222> LOCATION: (107)..(107)
<223> OTHER INFORMATION: n is a, c, g, or t
<220> FEATURE:
<221> NAME/KEY: misc_feature
<222> LOCATION: (116)..(116)
<223> OTHER INFORMATION: n is a, c, g, or t
<220> FEATURE:
```

```
<221> NAME/KEY: misc_feature
<222> LOCATION: (118)..(118)
<223> OTHER INFORMATION: n is a, c, g, or t

<400> SEQUENCE: 40
agatcagaga gttttgagca gtaaagccag cttccataat tatatgcttc aactaacaat      60
kagagccaca aattcacatc tacaattaca tttaaccttc atttgtnaaa aaaaantngc     120
a                                                                    121

<210> SEQ ID NO 41
<211> LENGTH: 121
<212> TYPE: DNA
<213> ORGANISM: Cucumis melo

<400> SEQUENCE: 41
ttctattctc ctttcttagc actgcagaga aatccggcac cgattgcgcc accgtagcgg      60 wcctttcct tacagtctcc gaacccagaa atttaatttg cttcttgggc gggggggtgg     120
a                                                                    121

<210> SEQ ID NO 42
<211> LENGTH: 121
<212> TYPE: DNA
<213> ORGANISM: Cucumis melo
<220> FEATURE:
<221> NAME/KEY: misc_feature
<222> LOCATION: (111)..(111)
<223> OTHER INFORMATION: n is a, c, g, or t

<400> SEQUENCE: 42 actttgctg aaactcatag cataattatt atttgtatac ctatatatcc cttcattgga      60
wgctacttag cttattctt ttattggttt ctttgagatt aattgctagc ntcagttctc     120
a                                                                    121

<210> SEQ ID NO 43
<211> LENGTH: 121
<212> TYPE: DNA
<213> ORGANISM: Cucumis melo

<400> SEQUENCE: 43
taggggaagg ctctaacaaa tgaagaggtt ggagaatcac aaactagagg accacgacca      60
rtggacaagt tgatcctagg tagaaataat aaaaagtcaa tgcattcgaa cttgagaagg     120
t                                                                    121

<210> SEQ ID NO 44
<211> LENGTH: 121
<212> TYPE: DNA
<213> ORGANISM: Cucumis melo
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t

<400> SEQUENCE: 44
aagttctttt ggattcnttn ggttttatta aatggggaat gccaatcaat gctttgcaat      60
sgaaaggagg ggttgcattc tgataggact cctatctttg atatgaaatt cttctttatt     120
t                                                                    121
```

-continued

<210> SEQ ID NO 45
<211> LENGTH: 121
<212> TYPE: DNA
<213> ORGANISM: Cucumis melo
<220> FEATURE:
<221> NAME/KEY: misc_feature
<222> LOCATION: (26)..(26)
<223> OTHER INFORMATION: n is a, c, g, or t

<400> SEQUENCE: 45
cgaagctgtg gaaggtttct gtgccnaaaa agaaaggttg ggtcttaaag ctggatttgg      60
waaaggcctt tgatcatgtg gattgggtgt tccttgaaaa gttgcttctt tgtaaaatgt     120
t                                                                    121

<210> SEQ ID NO 46
<211> LENGTH: 121
<212> TYPE: DNA
<213> ORGANISM: Cucumis melo

<400> SEQUENCE: 46
ataagaggac cctacaagta cttgaaaatt tctagatttc ttttgaaatt ctaatccact      60
rggaaacttc attttgtgc tatcttagat tcttattact tgcttccttt gattcttata     120
c                                                                    121

<210> SEQ ID NO 47
<211> LENGTH: 121
<212> TYPE: DNA
<213> ORGANISM: Cucumis melo
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t

<400> SEQUENCE: 47
tgtataaatn ncaaagtact attgcactnc caatacaaga tagaggaaat ttctcccata      60
wttgcaaact acgatttctt acttggcatc agagcattga aatggccaac atcgtctccn     120
t                                                                    121

<210> SEQ ID NO 48
<211> LENGTH: 121
<212> TYPE: DNA
<213> ORGANISM: Cucumis melo

<400> SEQUENCE: 48
tttcaaggag ttgggactca catttgcatc tgatggaatt tgcatataat aacagttatc      60
rtgctaccat tgacatgaca ccattttaag ctttgtgcga taagtgttgc agattctcta     120
t                                                                    121

<210> SEQ ID NO 49
<211> LENGTH: 121
<212> TYPE: DNA
<213> ORGANISM: Cucumis melo

<400> SEQUENCE: 49
tcatgaacgt gaacttcgaa tggcagaccc cgtaggccct catttcatcc attcattttc     60
rttcccattc tttgtctgat tgtgttggct gtcacggcgc catagatttt gtttgtggtt    120
c                                                                    121

<210> SEQ ID NO 50
<211> LENGTH: 121
<212> TYPE: DNA
<213> ORGANISM: Cucumis melo
<220> FEATURE:
<221> NAME/KEY: misc_feature
<222> LOCATION: (102)..(102)
<223> OTHER INFORMATION: n is a, c, g, or t

<400> SEQUENCE: 50
tccgattgga tggtggaggt ggagggcgct aaactgtatt atcaagggac tttttgctta     60
ytttcccatt ggacactccc ttaatatcaa cggtccattc cncacgcata atttcgatga    120
t                                                                    121

<210> SEQ ID NO 51
<211> LENGTH: 121
<212> TYPE: DNA
<213> ORGANISM: Cucumis melo

<400> SEQUENCE: 51
ttcattctga gaagcattga cttaaaattc atgtgctgtg cacagacata ctgctactat     60
kctccttgta tcagaagcca aacacatagg ctgggacttg tcaaagaatc tacctaactg    120
c                                                                    121

<210> SEQ ID NO 52
<211> LENGTH: 121
<212> TYPE: DNA
<213> ORGANISM: Cucumis melo

<400> SEQUENCE: 52
gaattcctta tcaaatattg caatttcaga ccaattactc tcacaagctt gacttacaag     60
kttgttgcca aggtgctgtc cgaaagactc aaaggcaatt ccttgcatca ttgcccctc    120 a                                                                    121

<210> SEQ ID NO 53
<211> LENGTH: 121
<212> TYPE: DNA
<213> ORGANISM: Cucumis melo

<400> SEQUENCE: 53
gaatactcat taaattcctt gttcaaagaa caccaagctg ctgcatttct ttttgcagtg     60
yccgaagttt cagaccagcc ccttgacttg ttatgaaaga ttcgttgatt acgttcaaac    120
c                                                                    121

<210> SEQ ID NO 54
<211> LENGTH: 121
<212> TYPE: DNA
<213> ORGANISM: Cucumis melo

<400> SEQUENCE: 54
agcgcttgaa aaactgagaa gattgggaac tagaatctga cctatttata ttaatcggtt     60
saaggagttg agagcaatgg gcttccaaca agtttgggtt gttcttggta agttgagacc    120

```
t                                                                    121

<210> SEQ ID NO 55
<211> LENGTH: 121
<212> TYPE: DNA
<213> ORGANISM: Cucumis melo
<220> FEATURE:
<221> NAME/KEY: misc_feature
<222> LOCATION: (5)..(5)
<223> OTHER INFORMATION: n is a, c, g, or t

<400> SEQUENCE: 55
ttttngtccc cttgtattca tttccaagag attgtcttca ttggagggca gccaaccaat      60
yagatagata atgaacttca attaagccaa aagaactctg caatccttga caatggaagt    120
t                                                                    121

<210> SEQ ID NO 56
<211> LENGTH: 121
<212> TYPE: DNA
<213> ORGANISM: Cucumis melo

<400> SEQUENCE: 56
aaagtaagtt gaattagtta catttgggag acaaaaacac aagctctttt cacatatccc     60
kggcagccaa aagaagaaag aatctgaata cagagttagt taatgactcc ggggtgccca    120
c                                                                    121

<210> SEQ ID NO 57
<211> LENGTH: 99
<212> TYPE: DNA
<213> ORGANISM: Cucumis melo

<400> SEQUENCE: 57
ttgaaggttt ggaagaacca tcaccagcaa agaaataaaa aatctcctca tgtaagtcaa     60
yccaatcatc tcaagaaga caaaataaaa ctttgcaaa                             99

<210> SEQ ID NO 58
<211> LENGTH: 103
<212> TYPE: DNA
<213> ORGANISM: Cucumis melo

<400> SEQUENCE: 58
gagtattttc ataattttgt tgtgcatgat tgatgtggca ttaaggtttt attaggaggc     60
yatcttactt aaatcgtcaa taacatttag atgtgattaa tct                      103

<210> SEQ ID NO 59
<211> LENGTH: 121
<212> TYPE: DNA
<213> ORGANISM: Cucumis melo

<400> SEQUENCE: 59
gaatgaaaca ttagtcatgc agtggttatc caagaactgc catactgttt tgaacaatct     60
wccaacatca attgaagaag acgatcagct tctgtgcaat atcgccaaag tccaagattt    120
g                                                                    121

<210> SEQ ID NO 60
<211> LENGTH: 121
<212> TYPE: DNA
<213> ORGANISM: Cucumis melo
```

```
<400> SEQUENCE: 60
gaaagggtgc tagcagttct tcatcttcat atgagcaaga gatgcattcc agagaggttt    60
kcgaactaag acctaacctt gaaaatgctc aataattaat tgacgaacaa tgaagaacgt   120
c                                                                    121

<210> SEQ ID NO 61
<211> LENGTH: 121
<212> TYPE: DNA
<213> ORGANISM: Cucumis melo

<400> SEQUENCE: 61
aagatgaaga aaataacaat aaggaagata taaaaaatga tcattactga aagtgagttg    60
ragccaaatc aggcgaaaaa tcttaatctt aaaaatttaa aaaccactac aaacttggaa   120
a                                                                    121

<210> SEQ ID NO 62
<211> LENGTH: 121
<212> TYPE: DNA
<213> ORGANISM: Cucumis melo

<400> SEQUENCE: 62
ttgatcgtgg aatgttcaca catgaagata ttaatggcgc agacctttg gttcaataat     60 yggttgcatt ggaatttgta tagtgaaact tgtgtggttt gaaggttgca ataatgaga    120 t                                                                    121

<210> SEQ ID NO 63
<211> LENGTH: 121
<212> TYPE: DNA
<213> ORGANISM: Cucumis melo
<220> FEATURE:
<221> NAME/KEY: misc_feature
<222> LOCATION: (26)..(26)
<223> OTHER INFORMATION: n is a, c, g, or t

<400> SEQUENCE: 63
ttgctcttct ttttggacag aatganggga gtatgagttg gagtacctct caggaatttc    60
mcctttgaat taggcattga gaagctagag tattcaaagt gttgaagatg agaggattca   120
g                                                                    121

<210> SEQ ID NO 64
<211> LENGTH: 121
<212> TYPE: DNA
<213> ORGANISM: Cucumis melo
<220> FEATURE:
<221> NAME/KEY: misc_feature
<222> LOCATION: (4)..(4)
<223> OTHER INFORMATION: n is a, c, g, or t

<400> SEQUENCE: 64
gatngtttct tcatcaataa ggtgtgggat taaatctttg acaacacaag aatcacccga    60
saagcatgca ctttctttga tcatttccca gagtttggag aaaggtggaa acattgtcct   120
t                                                                    121

<210> SEQ ID NO 65
<211> LENGTH: 121
<212> TYPE: DNA
<213> ORGANISM: Cucumis melo

<400> SEQUENCE: 65
```

-continued atgggccaaa aatcacaact tagcacccac ccatctttac caatgaattt cgacacttcc    60
rgtcttcctt gatctagctc cccaaagtta tgaaagaaac catcttctgg acctcttata    120
a    121

<210> SEQ ID NO 66
<211> LENGTH: 121
<212> TYPE: DNA
<213> ORGANISM: Cucumis melo
<220> FEATURE:
<221> NAME/KEY: misc_feature
<222> LOCATION: (15)..(15)
<223> OTHER INFORMATION: n is a, c, g, or t

<400> SEQUENCE: 66
cacaatttac ctcancacat cctttttat ttttcacgac acaacgtctt cattggtagt    60
rtcattaaaa cccattttc tagtagtgat ttctaatttt aggttacatg caagagaaaa    120
g    121

<210> SEQ ID NO 67
<211> LENGTH: 121
<212> TYPE: DNA
<213> ORGANISM: Cucumis melo

<400> SEQUENCE: 67
ttcaatacca gtgtcttctc tcgatgccgg tggcactgtt ccaggccaac ctgagctcct    60
ycctcccaac tccctcgacg actcgttccg gagtgcatcc ttctccaaag ccatagatca    120
t    121

<210> SEQ ID NO 68
<211> LENGTH: 121
<212> TYPE: DNA
<213> ORGANISM: Cucumis melo

<400> SEQUENCE: 68
aaataagaat aatgatgcat attatttacc gcctccaagg aaaaaaagc acatttgggg    60 ytgtttggcc caacttcaaa tgggtgctcc tgtgtctggg acttcaatta caatatatgg    120
t    121

<210> SEQ ID NO 69
<211> LENGTH: 121
<212> TYPE: DNA
<213> ORGANISM: Cucumis melo

<400> SEQUENCE: 69
aaaaggaatg gagcttgcaa aggttcttag agatgcgcag gaatgcaata gttcagatac    60
raagcatcaa gaatgcaaga agccggaaca gcagaatggt tctacaactg ctaatgcgac    120
t    121

<210> SEQ ID NO 70
<211> LENGTH: 121
<212> TYPE: DNA
<213> ORGANISM: Cucumis melo

<400> SEQUENCE: 70
aggcaatctc gaggattctt gtcgtctgag aggaatgcct tctccaccac taaatccatc    60
ytcctcggca tgcttagaga gccgtattga taagtttgcc gctggacctg tatcaatttg    120
c                                                                    121

<210> SEQ ID NO 71
<211> LENGTH: 121
<212> TYPE: DNA
<213> ORGANISM: Cucumis melo

<400> SEQUENCE: 71
tttactttca acggtggaa gaaggtgttg aacctgacca tttcactttt cctcgtgtgc      60
wcaaggcctg tggtggcatt gggtcgattc aaactggaga ggcggtgcat cggcatgttg    120
t                                                                   121

<210> SEQ ID NO 72
<211> LENGTH: 121
<212> TYPE: DNA
<213> ORGANISM: Cucumis melo

<400> SEQUENCE: 72
attttggtcc ataaccaaag tctcaggaga gctgtgcact aaaatgctag ataatttacg     60
kagtgctcag gaatgctata atgcaaaagg aacatataag atccatagta gaaaccatgt   120
t                                                                   121

<210> SEQ ID NO 73
<211> LENGTH: 121
<212> TYPE: DNA
<213> ORGANISM: Cucumis melo

<400> SEQUENCE: 73
gtttaaccaa ttataagtca attgaataag atcagcatca tgacaaataa aataagctca     60
ytcagaaatc aacataggcc tactgatcaa gaagcaacct ctaagcacat attttcattt   120
t                                                                   121

<210> SEQ ID NO 74
<211> LENGTH: 121
<212> TYPE: DNA
<213> ORGANISM: Cucumis melo
<220> FEATURE:
<221> NAME/KEY: misc_feature
<222> LOCATION: (108)..(108)
<223> OTHER INFORMATION: n is a, c, g, or t

<400> SEQUENCE: 74
attgggtcca ttgttttttgt ttctaagata atcttccaaa cttcaagatt agcaattcca    60
rtccttgacc tccatttcgg tccttgagaa cgtgatggaa aaaaaatnat acaattcaaa   120
a                                                                   121

<210> SEQ ID NO 75
<211> LENGTH: 121
<212> TYPE: DNA
<213> ORGANISM: Cucumis melo

<400> SEQUENCE: 75
taaaaggtca atcagaaact ccatgaacct ctcgcaatac aaaatacaag cattgtctcc     60
mtctatcaac ccattggcat caacagattg actgtttgca tcatctgaat tattctgagg   120
g                                                                   121

<210> SEQ ID NO 76
<211> LENGTH: 121

<212> TYPE: DNA
<213> ORGANISM: Cucumis melo

<400> SEQUENCE: 76
ggccaaacac gtagagattt ttgtacttct gacctagaat cactagacac aatgtcacga    60
rcatctgaaa ttgaggaaga attgctaatc tcaagaaatg attgggtatc tgcggaacag   120
g                                                                  121

<210> SEQ ID NO 77
<211> LENGTH: 121
<212> TYPE: DNA
<213> ORGANISM: Cucumis melo

<400> SEQUENCE: 77
ctcttactaa aaagagatc agtgtatgtc ttccttcttc gttttctat cactttaagg      60
ytgattctat tcggttcaaa gctatgtttg cactctttcc tacctttttc gttaatattt   120
g                                                                  121

<210> SEQ ID NO 78
<211> LENGTH: 121
<212> TYPE: DNA
<213> ORGANISM: Cucumis melo

<400> SEQUENCE: 78
agtggcacat gttttggttc ggactttgtt atgtgaaaca ataaaatgt tcattaattg     60
mgtttgcatt gcattattta caagtattac tcaatgtatt atatgaaacc ttaggggaat   120
t                                                                  121

<210> SEQ ID NO 79
<211> LENGTH: 121
<212> TYPE: DNA
<213> ORGANISM: Cucumis melo

<400> SEQUENCE: 79
aaggaattct atgtttgtag tttgaatgtt tggtgaagag agtgcaaaaa ggtcctccaa    60
sgtaagattt aatacccact gtaagcagat tttttgtaga cgataatata taaagcaatc   120
a                                                                  121

<210> SEQ ID NO 80
<211> LENGTH: 95
<212> TYPE: DNA
<213> ORGANISM: Cucumis melo
<220> FEATURE:
<221> NAME/KEY: misc_feature
<222> LOCATION: (87)..(92)
<223> OTHER INFORMATION: n is a, c, g, or t

<400> SEQUENCE: 80
aaaaggggga aaaacctcaa agcttacctt cactrcctcg tccagctcaa agcccagcag    60
cagcaacgcc tgtaataatg aacagtnnnn nnttt                               95

<210> SEQ ID NO 81
<211> LENGTH: 121
<212> TYPE: DNA
<213> ORGANISM: Cucumis melo

<400> SEQUENCE: 81
atcctaagct accaacttta attgctttga gaaatggtaa cttttttctc cattcatagc    60

```
ytgaaatgaa tttgtctgag ttgctcaatt ctataaatat ggtatggtcg tccattttat    120
c                                                                    121

<210> SEQ ID NO 82
<211> LENGTH: 121
<212> TYPE: DNA
<213> ORGANISM: Cucumis melo

<400> SEQUENCE: 82 cattttttgat gaatatgtat atgtagactt gaacaagtac aaaataccttt agcaaaaagg   60 mtgtcaaaca gtgaacagaa atatttatca ttcttattaa ataagaaaat atacctctttt   120 t                                                                    121

<210> SEQ ID NO 83
<211> LENGTH: 121
<212> TYPE: DNA
<213> ORGANISM: Cucumis melo

<400> SEQUENCE: 83
agtaaattct gcttttaat ggttttctta gggggaaga gggagatgag aactaatgat      60
kacttgcgtg aattcacaca aatctagata caagtgcatc ttacagtttc tgtggggcaa   120
g                                                                    121

<210> SEQ ID NO 84
<211> LENGTH: 121
<212> TYPE: DNA
<213> ORGANISM: Cucumis melo

<400> SEQUENCE: 84
ccattgagca acgcagtgag agaattaaaa gaaaatctag cgttgtgatt aaactcgaag    60
mggagttctc tgaccttgtt agtcccttaa atatctccag tcctggaaag gagatttcgg   120
c                                                                    121

<210> SEQ ID NO 85
<211> LENGTH: 121
<212> TYPE: DNA
<213> ORGANISM: Cucumis melo

<400> SEQUENCE: 85
tcaagatgcc gatcttttat tctttattgt tcgtaattta taccgtgatc ttcagtctcc    60
ragagcactg aggttggaaa cagatgatgt caatgctccc cagcggcttc ccctttttgaa  120 a                                                                    121

<210> SEQ ID NO 86
<211> LENGTH: 121
<212> TYPE: DNA
<213> ORGANISM: Cucumis melo
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t

<400> SEQUENCE: 86
tcgnaaaccg attccacttg gggtgtgcca natggctgtt cctgattggc ttcgagacgt    60
yagccatctc accaccccga tgctccacag atcagcgagt tccaactacc tgttgttgta   120
```

<210> SEQ ID NO 87
<211> LENGTH: 121
<212> TYPE: DNA
<213> ORGANISM: Cucumis melo

<400> SEQUENCE: 87
tagcgtaatt cgatacttca tataggtagt tgtagcgtat ttgttatcta ccatttgttg    60
wgtggctaag tcaagtttat aggaggctta ttcacataca tatagattaa tgtaccttgt   120
c                                                                    121

<210> SEQ ID NO 88
<211> LENGTH: 121
<212> TYPE: DNA
<213> ORGANISM: Cucumis melo

<400> SEQUENCE: 88
caaaaacctg tgatcgtcaa agaattccgt caagttttga atctcgatat actcaagacc    60
ygcttctcta gccaacctga gtgagttata gccaccattt ggataaattc attcagatat   120
t                                                                    121

<210> SEQ ID NO 89
<211> LENGTH: 121
<212> TYPE: DNA
<213> ORGANISM: Cucumis melo

<400> SEQUENCE: 89
ccaagtatgc cacaaaccac cgccatatgt ctgcacattg accattagac aattacactt    60
sttcgacgaa gacttcggct ttaattttag gcatgggcta tctgtgtgag cagcaataac   120
a                                                                    121

<210> SEQ ID NO 90
<211> LENGTH: 121
<212> TYPE: DNA
<213> ORGANISM: Cucumis melo
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(14)
<223> OTHER INFORMATION: n is a, c, g, or t
<220> FEATURE:
<221> NAME/KEY: misc_feature
<222> LOCATION: (16)..(19)
<223> OTHER INFORMATION: n is a, c, g, or t
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (25)..(27)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (36)..(38)
<223> OTHER INFORMATION: n is a, c, g, or t

```
<400> SEQUENCE: 90
naaaaaannn nnnntnnnna nnaannnccc nttttnnntc atcacctaca gtggttcatg      60
rtttcaaaat accttgtttc ctgaattata ataagctttg ttaattaaca aaggtttcca     120
c                                                                    121

<210> SEQ ID NO 91
<211> LENGTH: 121
<212> TYPE: DNA
<213> ORGANISM: Cucumis melo

<400> SEQUENCE: 91
catagttcta gccgaccttg ccaagtcgac cagaactatg gtaataaaaa ttgactagaa      60
watcagacgc ataattcaag aacatttcaa aagaatttaa gaaactacct tcttgatcct    120
g                                                                    121

<210> SEQ ID NO 92
<211> LENGTH: 121
<212> TYPE: DNA
<213> ORGANISM: Cucumis melo

<400> SEQUENCE: 92
aagaaattat ttttcagaat ggacatgatg ataaataaat gatttaactg gattcaggaa      60
rgagtatttc gagatctcat gggcaggctt gaggtcaatg gtggagccat catttgctga    120
a                                                                    121

<210> SEQ ID NO 93
<211> LENGTH: 121
<212> TYPE: DNA
<213> ORGANISM: Cucumis melo
<220> FEATURE:
<221> NAME/KEY: misc_feature
<222> LOCATION: (4)..(5)
<223> OTHER INFORMATION: n is a, c, g, or t

<400> SEQUENCE: 93
aganngtagt attgaatttg tgatctactt actgaaggta gaagaattat aagttgtcca      60
mccatcaacg acgttatggt tcccggtgat gatggttcgg ttaatgccgt ctccaataag    120
c                                                                    121

<210> SEQ ID NO 94
<211> LENGTH: 121
<212> TYPE: DNA
<213> ORGANISM: Cucumis melo
<220> FEATURE:
<221> NAME/KEY: misc_feature
<222> LOCATION: (95)..(95)
<223> OTHER INFORMATION: n is a, c, g, or t
<220> FEATURE:
<221> NAME/KEY: misc_feature
<222> LOCATION: (106)..(106)
<223> OTHER INFORMATION: n is a, c, g, or t

<400> SEQUENCE: 94
tcatagttac tatacatttg gctacaattt tcattgttta tagtttcaat tcaactatga      60
raccatacta aaatcgtatt gaacaaaact tcaantcttc acgatntaga tattacttttt   120 a                                                                    121

<210> SEQ ID NO 95
<211> LENGTH: 121
```

```
<212> TYPE: DNA
<213> ORGANISM: Cucumis melo

<400> SEQUENCE: 95
tcatgtttgt tggtaagatt gtttgcttca tttttttgat ggcttataat ttcaggctcc      60
wcaaagcagt gctgatgcta cagggaattc tgatatcgat atccctcctg aattggtgaa     120
t                                                                    121

<210> SEQ ID NO 96
<211> LENGTH: 121
<212> TYPE: DNA
<213> ORGANISM: Cucumis melo

<400> SEQUENCE: 96
aaattatgca ttctaacaaa gaagacttaa tcatggcggc tgatatggtg tcccttcatc      60
rcactgatta tttgtttacc gacggggctc cggctccggc agcagtaggc gatagccgac     120
t                                                                    121

<210> SEQ ID NO 97
<211> LENGTH: 121
<212> TYPE: DNA
<213> ORGANISM: Cucumis melo

<400> SEQUENCE: 97
attccatgaa ttgacaagtt gaacaatttg ggtgtcctga actcttcttc tcttgtgcat      60
yctaagtggt cacattgtga agaatattta ttccctgttt gttggatttt gttttagtgg     120
t                                                                    121

<210> SEQ ID NO 98
<211> LENGTH: 100
<212> TYPE: DNA
<213> ORGANISM: Cucumis melo

<400> SEQUENCE: 98
ggggacggga gaggggggaga gaagaattaa ggaaggaaay agagagagac atggagatgg     60
gagctttgtt atatttcgga gtttggtgat aatggcggag                          100

<210> SEQ ID NO 99
<211> LENGTH: 121
<212> TYPE: DNA
<213> ORGANISM: Cucumis melo

<400> SEQUENCE: 99
ccacaagagg gccctgccat taaagtagct tctgagaaaa tctttagctt tcttgacaat      60
rtgcaggcag agttggaaag tcttaatggt aattctgaag ctttcttcca ggtgtgcgac     120
a                                                                    121

<210> SEQ ID NO 100
<211> LENGTH: 121
<212> TYPE: DNA
<213> ORGANISM: Cucumis melo

<400> SEQUENCE: 100
aactcgactt taaattgggt caacggtgat ttaacatgaa gttgcagtaa gagttgctaa      60
sttgaaatct ttgcaacacc atctcttatt catcaacctc taaccattaa acacaagaaa    120
a                                                                    121
```

<210> SEQ ID NO 101
<211> LENGTH: 121
<212> TYPE: DNA
<213> ORGANISM: Cucumis melo
<220> FEATURE:
<221> NAME/KEY: misc_feature
<222> LOCATION: (105)..(105)
<223> OTHER INFORMATION: n is a, c, g, or t

<400> SEQUENCE: 101
caaaatctct gtcagttcaa agtgagtcta aatcgaaact ccaccggttt tcttctgagc    60
ygattcgcct taatggggga caagctgctg gattccattg aaaantattc tgccattact   120
t                                                                  121

<210> SEQ ID NO 102
<211> LENGTH: 121
<212> TYPE: DNA
<213> ORGANISM: Cucumis melo
<220> FEATURE:
<221> NAME/KEY: misc_feature
<222> LOCATION: (27)..(27)
<223> OTHER INFORMATION: n is a, c, g, or t

<400> SEQUENCE: 102
attgttgagg ggcaaggagt gtttacngtc acgatggtaa ggcgagctac atgaaggttc    60
rcctcttgcc cgatcaggga agtctgttcc tgcactgtca agactcatcc ttgaatcagc   120
a                                                                  121

<210> SEQ ID NO 103
<211> LENGTH: 121
<212> TYPE: DNA
<213> ORGANISM: Cucumis melo

<400> SEQUENCE: 103
aacgtaacgg tgactaaatt ggacagaaaa tgaaccatgg agcaaagtta atttcatagc    60
yagggatgct cactggtgtt tttgaactgt aatctcgtga ggatattgat gccattttgt   120
t                                                                  121

<210> SEQ ID NO 104
<211> LENGTH: 121
<212> TYPE: DNA
<213> ORGANISM: Cucumis melo

<400> SEQUENCE: 104
caaacatctt tgaaactttt tcacaccttg aagtcttaaa tttgcatgtg ccatctgtaa    60
ytgaaatgct ataaatttca tgtgattata tctgatattt tcagtggctg gattccttt   120 c                                                                  121

<210> SEQ ID NO 105
<211> LENGTH: 121
<212> TYPE: DNA
<213> ORGANISM: Cucumis melo

<400> SEQUENCE: 105
cttcgagcct ctgcggaaat gcttggaaaa ggtgggttcg gaacttcgta caaggcgatt    60
ytggacgacg gcaatgtggt ggcggtgaaa cggctgaaag atgcgcaggt tggagggaaa   120
c                                                                  121

```
<210> SEQ ID NO 106
<211> LENGTH: 121
<212> TYPE: DNA
<213> ORGANISM: Cucumis melo

<400> SEQUENCE: 106
ttgagggact tgcaggaatt gtgaataaaa gccaatcctc tagctgctcc agcggcgatc      60
ytcaacctcg ttgtccaatc caacggcgtt cgtccagggc ctctgtttcc tatcaaacag     120
t                                                                    121

<210> SEQ ID NO 107
<211> LENGTH: 111
<212> TYPE: DNA
<213> ORGANISM: Cucumis melo

<400> SEQUENCE: 107
atgcacagaa atgtatgtgg cacaagaaac agtctgttaa tccttccaat tttagaacac      60
raacttccaa taatttacca tcagttttca ttgaaatatt cagatatgca t              111

<210> SEQ ID NO 108
<211> LENGTH: 121
<212> TYPE: DNA
<213> ORGANISM: Cucumis melo

<400> SEQUENCE: 108
ggcttgtgtt ctcttctagt taaactgaag atgaactaat gtagaatgtc aaaggtttgc      60
ygtaggtgac gtatatgttg tgaagtaaaa tttgttttta aacgtaagtg ttgttcagtg     120
a                                                                    121

<210> SEQ ID NO 109
<211> LENGTH: 121
<212> TYPE: DNA
<213> ORGANISM: Cucumis melo

<400> SEQUENCE: 109
aagaaagtgg gaataaaata aagtaccgat cagaaaagtg ctagaaatta agaaatgtta      60
wagcaagata gagctcatta gtagtggtcg actccactga ttaaagagtt ccgtagaaaa     120
a                                                                    121

<210> SEQ ID NO 110
<211> LENGTH: 91
<212> TYPE: DNA
<213> ORGANISM: Cucumis melo

<400> SEQUENCE: 110
cctgagaatt caccccacc gccaccatca rcacctccag aaacctcacc tccctcccca      60
gcatcaatac ctcctagaaa ttcaccgcca c                                    91
```

METHODS AND COMPOSITIONS FOR PRODUCING PLANTS WITH ELEVATED BRIX

BACKGROUND OF THE INVENTION

This application claims the priority of U.S. Provisional Appl. Ser. No. 61/642,978, filed May 4, 2012, the entire disclosure of which is incorporated herein by reference.

INCORPORATION OF SEQUENCE LISTING

The sequence listing that is contained in the file named "SEMB005US_ST25.txt", which is 39 kilobytes as measured in Microsoft Windows operating system and was created on May 1, 2013, is filed electronically herewith and incorporated herein by reference.

FIELD OF THE INVENTION

The present invention relates to the field of plant breeding and, more specifically, to methods and compositions for producing melon plants with elevated Brix.

DESCRIPTION OF RELATED ART

Melon fruits are highly appreciated worldwide and are often eaten as a fresh product. Melons are members of the gourd family (Cucurbitaceae), a class of trailing annual vines that also includes squash, pumpkin and cucumber. They have large broad leaves, stems covered in light prickles and small yellow flowers. The fruit themselves are soft fleshed with a central cavern containing seeds, surrounded by a thick protective rind.

Taxonomically, melons are broadly divided into two groups: watermelons (species *Citrullus lanatus*) and muskmelons (species *Cucumis melo* L.). *C. melo* includes a wide variety of cultivars producing fruits of different shape, external appearance and flesh color, including such melons as Canary, Cantaloupe (including Western Shipper, North American and Charentais types), Casaba, Hami, Honeydew, Navajo Yellow, Piel de Sapo, Santa Claus, Sugar melon, Ambrosia, Bailan, Galia, Ogen, Persian, and Sharlyn.

One important goal of melon breeding is to combine various desirable traits in a single variety/hybrid. While breeding efforts to date have provided a number of useful melon lines and varieties with beneficial traits, there remains a need in the art for new lines and varieties with further improved traits and methods for their production. In many cases, such efforts have been hampered by difficulties in identifying and using alleles conferring beneficial traits.

SUMMARY OF THE INVENTION

The present invention overcomes limitations in the prior art by providing a *Cucumis melo* plant comprising at least a first introgressed chromosomal region conferring increased Brix content relative to a plant lacking the region, wherein the region is selected from the group consisting of a high Brix content contributing QTL defined by flanking markers NU0219671 and NU0218915 on *Cucumis melo* linkage group 4, a high Brix content contributing QTL defined by flanking markers NU0220114 and NU0219142 on *Cucumis melo* linkage group 10, and high Brix content contributing QTL defined by flanking markers NU0220114 and NU0220323 on *Cucumis melo* linkage group 10. Thus in certain embodiments the *Cucumis melo* plant comprises said high Brix content contributing QTL defined by flanking markers NU0219671 and NU0218915 and said high Brix content contributing QTL defined by flanking markers NU0220114 and NU0219142. In yet other embodiments, the *Cucumis melo* plant comprises said high Brix content contributing QTL defined by flanking markers NU0219671 and NU0218915 and said high Brix content contributing QTL defined by flanking markers NU0220114 and NU0220323.

In particular embodiments, the chromosomal region conferring increased Brix comprises the QTL found in *Cucumis melo* line BEST, a sample of seed of *Cucumis melo* line BEST having been deposited under ATCC Accession Number PTA-12263. The *Cucumis melo* plant may be further defined as one of the market class group consisting of Piel de Sapo, Juan Canary, Amarillo, Earl's Type, Honeydew, Orange-flesh honeydew, Hami Melon, Crenshaw, Casaba, Ananas, Galia, Charentais, Italian-type, and Western Shipper.

In some embodiments the *Cucumis melo* plant is homozygous for said chromosomal region. In other embodiments the plant produces fruit with an average Brix content of at least 9° Brix at fruit maturity. In certain embodiments the chromosomal region confers an increase of at least 1° Brix relative to an otherwise essentially isogenic plant lacking the chromosomal region. In additional embodiments the plant is inbred. In other embodiments the plant is hybrid.

In another aspect, the invention provides a seed of the *Cucumis melo* plant. In yet another aspect, the invention provides a part of such a plant. In some embodiments, the plant part is selected from the group consisting of a leaf, pollen, an ovule, a fruit, rootstock, a scion, and a cell. In a particular embodiment the plant part is a fruit.

A tissue culture of regenerable cells of the plant is also an aspect of the invention. In one embodiment the tissue culture comprises cells or protoplasts from a plant part selected from the group consisting of an embryo, a meristem, a cotyledon, pollen, a leaf, anthers, a root, a root tip, pistil, flower, seed and a stalk.

Another aspect of the present invention is a method of obtaining *Cucumis melo* germplasm comprising the steps of: a) assaying *Cucumis melo* plants or a seed thereof for the presence of at least a first genetic marker genetically linked to a chromosomal region conferring increased Brix content relative to a plant lacking the region, wherein the region is selected from the group consisting of a high Brix content contributing QTL defined by flanking markers NU0219671 and NU0218915 on *Cucumis melo* linkage group 4 and a high Brix content contributing QTL defined by flanking markers NU0220114 and NU0219142 on *Cucumis melo* linkage group 10; and b) selecting at least a first *Cucumis melo* plant or seed thereof comprising the genetic marker and the QTL that confers increased Brix content. In an embodiment of the method, the high Brix content contributing QTL on *Cucumis melo* linkage group 10 is defined by flanking markers NU0220114 and NU0220323. In certain embodiments, a high Brix content contributing allele has been inherited from *Cucumis melo* line BEST, or a progeny of any generation thereof comprising said allele from *Cucumis melo* line BEST, a sample of seed of said melon line BEST having been deposited under ATCC Accession Number PTA-12263.

In certain embodiments the first genetic marker is selected from the group consisting of NU0219671, NU0221090, NU0218604, NU0218684, NU0218148, NU0243432, NU0243324, NU0219095, NU0218257, NU0219354, NU0219672, NU0243607, NU0219118, NU0220372, NU0219774, NU0219889, NU0244419, NU0244478, NU0220446, NU0219650, NU0244718, NU0218943, NU0218512, NU0219136, NU0218860, NU0220597, NU0219475, NU0243542, NU0220825, NU0219448, NU0243629, NU0218829, NU0218923, NU0219448, NU0244022, NU0218871, NU0218901, NU0220173, NU0220684, NU0218887, NU0219803, NU0219004, NU0219642, NU0219025, NU0218757, NU0219015, NU0219386, NU0219676, NU0243281, NU0243478, NU0219177, NU0219316, NU0219426, NU0220839, NU0244508, NU0244665, NU0218187, NU0218513, NU0221036, NU0243535, NU0220613, NU0218306, NU0218509, NU0219086, NU0220451, NU0244507, NU0219425, NU0244254, NU0220942, NU0218848, NU0244041, NU0220202, NU0220577, and NU0218915.

In particular embodiments the first genetic marker is selected from the group consisting of NU0219671, NU0243432, NU0219672, NU0219774, NU0220446, NU0218512, NU0243542, NU0219676, NU0220613, NU0244254, NU0220202, and NU0218915. In certain embodiments of the method, the first genetic marker is selected from the group consisting of NU0219671 and NU0218915.

In some embodiments, the first genetic marker is selected from the group consisting of NU0220114, NU0219003, NU0219125, NU0220581, NU0220762, NU0220116, NU0220849, NU0218843, NU0220323, NU0220985, NU0244737, NU0219214, NU0218908, NU0244415, NU0220766, NU0243268, NU0218664, NU0219506, NU0220650, NU0219176, NU0219728, NU0244427, NU0219075, NU0243568, NU0220301, NU0243578, NU0218206, NU0218955, NU0219589, NU0221079, NU0219683, NU0219740, NU0218191, NU0219782, and NU0219142. In certain embodiments the first genetic marker is selected from the group consisting of NU0220114, NU0219125, NU0220323, NU0244737, NU0218664, NU0243568, NU0219683, and NU0219142. In particular embodiments the first genetic marker is selected from the group consisting of NU0220114 and NU0219142. In other embodiments, the first genetic marker is selected from the group consisting of NU0220114 and NU0220323.

In other embodiments, the method comprises assaying the *Cucumis melo* plants or a seed thereof for a high Brix content contributing QTL defined by flanking markers NU0219671 and NU0218915 on *Cucumis melo* linkage group 4 and a high Brix content contributing QTL defined by flanking markers NU0220114 and NU0219142 on *Cucumis melo* linkage group 10. In certain embodiments, the method comprises assaying the *Cucumis melo* plants or a seed thereof for a high Brix content contributing QTL defined by flanking markers NU0219671 and NU0218915 on *Cucumis melo* linkage group 4 and a high Brix content contributing QTL defined by flanking markers NU0220114 and NU0220323 on *Cucumis melo* linkage group 10. In some embodiments assaying the *Cucumis melo* plants may comprise PCR, single strand conformational polymorphism analysis, denaturing gradient gel electrophoresis, cleavage fragment length polymorphism analysis, TAQMAN assay, and/or DNA sequencing.

Another aspect of the invention is a method of *Cucumis melo* plant breeding comprising: a) assaying *Cucumis melo* plants or seeds that produce the plants for the presence of at least a first genetic marker genetically linked to a chromosomal region conferring increased Brix content relative to a plant lacking the region, wherein the region is a high Brix content contributing QTL defined by flanking markers NU0219671 and NU0218915 on *Cucumis melo* linkage group 4, or a high Brix content contributing QTL defined by flanking markers NU0220114 and NU0219142 on *Cucumis melo* linkage group 10; and b) selecting at least a first *Cucumis melo* plant or seed that produces the plant comprising the genetic marker and the QTL that confers increased Brix; and c) crossing the first *Cucumis melo* plant with itself or a second *Cucumis melo* plant to produce progeny *Cucumis melo* plants comprising the QTL that confers increased Brix.

In some embodiments of this method, the first genetic marker is selected from the group consisting of NU0219671, NU0221090, NU0218604, NU0218684, NU0218148, NU0243432, NU0243324, NU0219095, NU0218257, NU0219354, NU0219672, NU0243607, NU0219118, NU0220372, NU0219774, NU0219889, NU0244419, NU0244478, NU0220446, NU0219650, NU0244718, NU0218943, NU0218512, NU0219136, NU0218860, NU0220597, NU0219475, NU0243542, NU0220825, NU0219448, NU0243629, NU0218829, NU0218923, NU0243807, NU0244022, NU0218871, NU0218901, NU0220173, NU0220684, NU0218887, NU0219803, NU0219004, NU0219642, NU0219025, NU0218757, NU0219015, NU0219386, NU0219676, NU0243281, NU0243478, NU0219177, NU0219316, NU0219426, NU0220839, NU0244508, NU0244665, NU0218187, NU0218513, NU0221036, NU0243535, NU0220613, NU0218306, NU0218509, NU0219086, NU0220451, NU0244507, NU0219425, NU0244254, NU0220942, NU0218848, NU0244041, NU0220202, NU0220577, and NU0218915. In other embodiments, the first genetic marker is selected from the group consisting of NU0220114, NU0219003, NU0219125, NU0220581, NU0220762, NU0220116, NU0220849, NU0218843, NU0220323, NU0220985, NU0244737, NU0219214, NU0218908, NU0244415, NU0220766, NU0243268, NU0218664, NU0219506, NU0220650, NU0219176, NU0219728, NU0244427, NU0219075, NU0243568, NU0220301, NU0243578, NU0218206, NU0218955, NU0219589, NU0221079, NU0219683, NU0219740, NU0218191, NU0219782, and NU0219142.

The method may further comprise the step of: d) selecting a progeny plant comprising the QTL and crossing the progeny plant with itself or a third *Cucumis melo* plant to produce additional progeny plants. In certain embodiments of the method, step (d) may be repeated about 2-10 times. Repeating step (d) may further comprise, in at least one generation, assaying *Cucumis melo* progeny plants or seed thereof for the presence of a genetic marker genetically linked to said QTL.

In some embodiments, selecting the first *Cucumis melo* plant comprises selecting the plant based on the presence of a genetic marker selected from the group consisting of NU0219671, NU0243432, NU0219672, NU0219774, NU0220446, NU0218512, NU0243542, NU0219676, NU0220613, NU0244254, NU0220202, NU0218915, NU0220114, NU0219125, NU0220323, NU0244737, NU0218664, NU0243568, NU0219683, and NU0219142. In other embodiments the chromosomal region conferring increased Brix comprises a high Brix QTL found in *Cucumis melo* line BEST, wherein the QTL is defined by flanking markers NU0219671 and NU0218915 on *Cucumis melo* linkage group 4 or by flanking markers NU0220114 and NU0219142 on *Cucumis melo* linkage group 10; and wherein a sample of seed of melon line BEST has been deposited under ATCC Accession Number PTA-12263. In another embodiment, assaying the *Cucumis melo* plants comprises PCR, single strand conformational polymorphism analysis, denaturing gradient gel electrophoresis, cleavage fragment length polymorphism analysis, TAQMAN assay, and/or DNA sequencing.

DETAILED DESCRIPTION OF THE INVENTION

Figure 1:
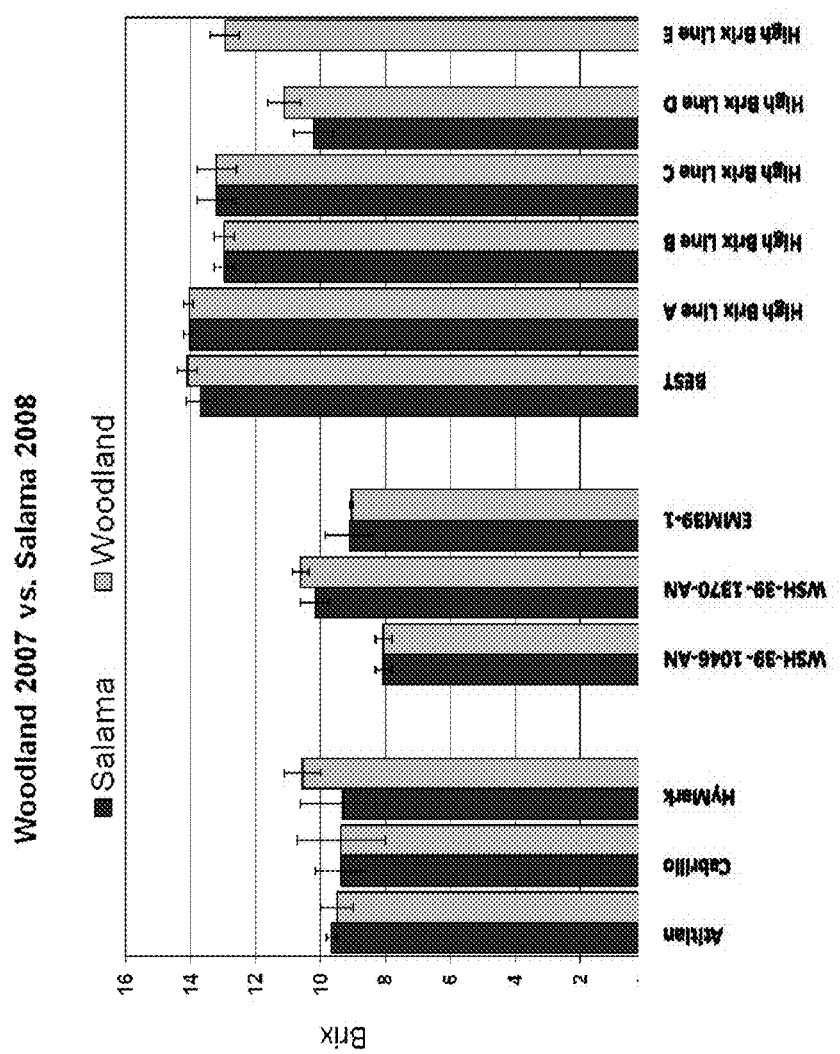
FIG. 1: Brix levels of the WSH controls and candidate Brix donor lines A-E, grown in two locations, with standard errors indicated.

The invention provides methods and compositions relating to plants, seeds and derivatives of *Cucumis melo* L, comprising introgressed chromosomal regions conferring elevated Brix. In particular, two introgressed QTL from melon line BEST are disclosed, and methods and compositions allowing for efficient marker-assisted selection to achieve progeny hybrid melon plants displaying enhanced fruit sweetness are provided. Two QTL were identified from donor line BEST which confer increased Brix. The QTL on LG4 is bounded by markers NU0219671 (map position 42.9067 cM) and NU0218915 (map position 63.5466 cM), while the QTL on LG10 is bounded by markers NU0220114 (map position 1.670227 cM) and NU0219142 (map position 14.3257 cM), including the region bounded by markers NU0220114 (map position 1.670227 cM) and NU0220323 (map position 4.48 cM). Progeny lines derived from line BEST displayed significantly elevated Brix levels as compared with parental and control lines in field trials performed at multiple growing locations.

Identification of these QTL allows for efficient marker-assisted selection of progeny melon lines for enhanced sweetness, i.e. elevated Brix, as well as deeper and/or earlier developing fruit color. A classical phenotypic breeding approach to select for such traits would require large replicated field trials in appropriate environments with extensive sampling of fruit, necessitating significant use of space, time, and labor, and could result in reduced ability to select other traits of importance to a breeding program, such as for disease resistance or other desired trait(s). Selection for Brix QTL with molecular marker tests on seedlings thus allows for large gains in breeding efficiency. These QTL may be introgressed into parental inbred lines to provide improved fruit quality in melons, for instance as grown in Central and South America for export to the US or elsewhere. The availability of high quality fruits with improved sweetness can lead to enhanced marketability and increased consumption, also improving human nutrition.

In particular embodiments, the invention provides markers genetically linked to the described QTL for Brix content which are located on *Cucumis melo* LG4 and LG10. In certain embodiments, the markers are within 20 cM, 10 cM, 5 cM, 3 cM, 1 cM, or less, of a QTL on melon LG4 or LG10 that allow for enhanced Brix. The presence of a given marker may be identified by use of well known techniques, such as by nucleic acid detection methods utilizing probes or primers comprising a sequence as disclosed herein. Genetic map position, physical map position, and allele and sequence information are given for selected genetic markers linked to QTL on LG4 and LG10 in Table 1 (SEQ ID NOs:1-110). For marker NU0218908, the estimated genetic map position (e.g. location relative to nearby markers) may be inaccurately estimated.

TABLE 1

Map position and allele information for selected genetic markers on melon LG4 and LG10 (SEQ ID NOs: 1-110); "n/a" = not available.

| Marker | Linkage Group ("LG") | Genetic map position (cM) | Physical map position (bp); | Favorable allele_BEST | Unfavorable allele_WSH-39-1046-AN | SEQ ID NO |
|---|---|---|---|---|---|---|
| NU0219671 | 4 | 42.90670132 | 9258434 | CC | AA | 1 |
| NU0221090 | 4 | 42.90670132 | 9270762 | | | 2 |
| NU0218604 | 4 | 43.0979374 | 9427935 | | | 3 |
| NU0218684 | 4 | 43.23036242 | 9616649 | | | 4 |
| NU0218148 | 4 | 44.23479447 | 9854150 | | | 5 |

TABLE 1-continued

Map position and allele information for selected genetic markers on
melon LG4 and LG10 (SEQ ID NOs: 1-110); "n/a" = not available.

| Marker | Linkage Group ("LG") | Genetic map position (cM) | Physical map position (bp); | Favorable allele_BEST | Unfavorable allele_WSH-39-1046-AN | SEQ ID NO |
|---|---|---|---|---|---|---|
| NU0243432 | 4 | 44.23479447 | 9965073 | GG | AA | 6 |
| NU0243324 | 4 | 44.79668663 | 10663097 | | | 7 |
| NU0219095 | 4 | 45.17459331 | 10798547 | | | 8 |
| NU0218257 | 4 | 45.20843312 | 10820633 | | | 9 |
| NU0219354 | 4 | 45.61944747 | n/a | | | 10 |
| NU0219672 | 4 | 45.7377921 | 11393641 | CC | TT | 11 |
| NU0243607 | 4 | 45.89414062 | 11394205 | | | 12 |
| NU0219118 | 4 | 47.56222556 | 13409958 | | | 13 |
| NU0220372 | 4 | 47.56222556 | 11920721 | | | 14 |
| NU0219774 | 4 | 49.07916075 | 13738760 | CC | GG | 15 |
| NU0219889 | 4 | 49.92630366 | 13741661 | | | 16 |
| NU0244419 | 4 | 49.92630366 | 14020679 | | | 17 |
| NU0244478 | 4 | 49.92630366 | 14025383 | | | 18 |
| NU0220446 | 4 | 50.15750223 | 14314960 | TT | AA | 19 |
| NU0219650 | 4 | 50.41420068 | 14393543 | | | 20 |
| NU0244718 | 4 | 50.41420068 | 14391032 | | | 21 |
| NU0218943 | 4 | 51.44499499 | 15014313 | | | 22 |
| NU0218512 | 4 | 52.56649468 | 15436556 | TT | AA | 23 |
| NU0219136 | 4 | 52.56649468 | 15661055 | | | 24 |
| NU0218860 | 4 | 53.42270279 | 15770285 | | | 25 |
| NU0220597 | 4 | 53.4428944 | 15948257 | | | 26 |
| NU0219475 | 4 | 53.45581073 | 16981336 | | | 27 |
| NU0243542 | 4 | 53.45581073 | 17307866 | GG | AA | 28 |
| NU0220825 | 4 | 53.45581073 | 16554223 | | | 29 |
| NU0219448 | 4 | 53.45581073 | 17207239 | | | 30 |
| NU0243629 | 4 | 53.45581073 | n/a | | | 31 |
| NU0218829 | 4 | 53.46405821 | 17298733 | | | 32 |
| NU0218923 | 4 | 53.46405821 | 17297098 | | | 33 |
| NU0243807 | 4 | 53.46405821 | 16342905 | | | 34 |
| NU0244022 | 4 | 53.46405821 | 16341935 | | | 35 |
| NU0218871 | 4 | 53.47027316 | 17208693 | | | 36 |
| NU0218901 | 4 | 53.55065617 | 16545065 | | | 37 |
| NU0220173 | 4 | 53.55415476 | 16337772 | | | 38 |
| NU0220684 | 4 | 53.62195987 | 15899732 | | | 39 |
| NU0218887 | 4 | 53.64086389 | 16752167 | | | 40 |
| NU0219803 | 4 | 53.88873817 | 16753311 | | | 41 |
| NU0219004 | 4 | 54.00461058 | 17341552 | | | 42 |
| NU0219642 | 4 | 54.00461058 | n/a | | | 43 |
| NU0219025 | 4 | 54.20812242 | 17536806 | | | 44 |
| NU0218757 | 4 | 54.31894245 | 17540043 | | | 45 |
| NU0219015 | 4 | 54.31894245 | 17342789 | | | 46 |
| NU0219386 | 4 | 54.45681139 | 18719229 | | | 47 |
| NU0219676 | 4 | 54.51656607 | n/a | AA | GG | 48 |
| NU0243281 | 4 | 54.51656607 | 18987560 | | | 49 |
| NU0243478 | 4 | 54.51656607 | 19132953 | | | 50 |
| NU0219177 | 4 | 54.51656607 | 19521311 | | | 51 |
| NU0219316 | 4 | 55.28134999 | 21180382 | | | 52 |
| NU0219426 | 4 | 55.28134999 | 21327981 | | | 53 |
| NU0220839 | 4 | 55.28134999 | 21092239 | | | 54 |
| NU0244508 | 4 | 55.28134999 | 21088377 | | | 55 |
| NU0244665 | 4 | 55.28134999 | 21180722 | | | 56 |
| NU0218187 | 4 | 55.28134999 | 21196877 | | | 57 |
| NU0218513 | 4 | 55.28134999 | 20650737 | | | 58 |
| NU0221036 | 4 | 55.28134999 | 20644745 | | | 59 |
| NU0243535 | 4 | 55.28134999 | 21329207 | | | 60 |
| NU0220613 | 4 | 55.8264394 | 21436236 | AA | GG | 61 |
| NU0218306 | 4 | 55.97274243 | 21568222 | | | 62 |
| NU0218509 | 4 | 55.97274243 | 21587099 | | | 63 |
| NU0219086 | 4 | 55.97274243 | 21558389 | | | 64 |
| NU0220451 | 4 | 55.97274243 | 21561207 | | | 65 |
| NU0244507 | 4 | 55.97274243 | 21662407 | | | 66 |
| NU0219425 | 4 | 58.92886945 | 21696482 | | | 67 |
| NU0244254 | 4 | 59.83874887 | 22253203 | CC | TT | 68 |
| NU0220942 | 4 | 59.87520725 | 22510081 | | | 69 |
| NU0218848 | 4 | 60.31911906 | 22835218 | | | 70 |
| NU0244041 | 4 | 60.41467622 | 24081543 | | | 71 |
| NU0220202 | 4 | 61.86643091 | n/a | TT | GG | 72 |
| NU0220577 | 4 | 63.48790382 | 24558770 | | | 73 |
| NU0218915 | 4 | 63.54660949 | 24769784 | GG | AA | 74 |
| NU0220114 | 10 | 1.670227256 | 383862 | CC | AA | 75 |
| NU0219003 | 10 | 1.825624361 | 494829 | | | 76 |
| NU0219125 | 10 | 2.460949526 | 537783 | TT | CC | 77 |
| NU0220581 | 10 | 2.529190171 | 555635 | | | 78 |

TABLE 1-continued

Map position and allele information for selected genetic markers on
melon LG4 and LG10 (SEQ ID NOs: 1-110); "n/a" = not available.

| Marker | Linkage Group ("LG") | Genetic map position (cM) | Physical map position (bp); | Favorable allele_BEST | Unfavorable allele_WSH-39-1046-AN | SEQ ID NO |
|---|---|---|---|---|---|---|
| NU0220762 | 10 | 3.802854385 | 659817 | | | 79 |
| NU0220116 | 10 | 4.140708555 | 671203 | | | 80 |
| NU0220849 | 10 | 4.140708555 | 668944 | | | 81 |
| NU0218843 | 10 | 4.47813079 | 762077 | | | 82 |
| NU0220323 | 10 | 4.47813079 | 735937 | GG | TT | 83 |
| NU0220985 | 10 | 5.74160713 | 838303 | | | 84 |
| NU0244737 | 10 | 5.74160713 | 839213 | AA | GG | 85 |
| NU0219214 | 10 | 5.74160713 | 870269 | | | 86 |
| NU0218908 | 10 | 5.74160713 | 1012622 | | | 87 |
| NU0244415 | 10 | 5.958658859 | 888018 | | | 88 |
| NU0220766 | 10 | 7.209687724 | 1039711 | | | 89 |
| NU0243268 | 10 | 7.209687724 | 1054026 | | | 90 |
| NU0218664 | 10 | 7.52970735 | 1111402 | TT | AA | 91 |
| NU0219506 | 10 | 7.950943936 | 1151696 | | | 92 |
| NU0220650 | 10 | 9.416408629 | 1239143 | | | 93 |
| NU0219176 | 10 | 9.418716215 | 1233075 | | | 94 |
| NU0219728 | 10 | 9.668938423 | 1282101 | | | 95 |
| NU0244427 | 10 | 9.668938423 | 1261013 | | | 96 |
| NU0219075 | 10 | 10.44636116 | 1338918 | | | 97 |
| NU0243568 | 10 | 10.44636116 | 1380818 | TT | CC | 98 |
| NU0220301 | 10 | 10.89127599 | 1420487 | | | 99 |
| NU0243578 | 10 | 10.98050134 | 1421936 | | | 100 |
| NU0218206 | 10 | 11.81903381 | 1465614 | | | 101 |
| NU0218955 | 10 | 11.81903381 | 1463213 | | | 102 |
| NU0219589 | 10 | 11.81903381 | 1391537 | | | 103 |
| NU0221079 | 10 | 12.41050087 | 1499072 | | | 104 |
| NU0219683 | 10 | 12.60551646 | 1556982 | TT | CC | 105 |
| NU0219740 | 10 | 12.60551646 | 1557750 | | | 106 |
| NU0218191 | 10 | 12.60551646 | 1604728 | | | 107 |
| NU0219782 | 10 | 14.28348493 | 1671415 | | | 108 |
| NU0219142 | 10 | 14.3257025 | 1676663 | TT | AA | 109 |
| NU0218502 | 10 | 18.82 | n/a | GG | AA | 110 |

In some embodiments, the markers used to follow the presence of any of these QTL of LG4 and/or LG10 are selected from the group consisting of: NU0219671, NU0218915, NU0220114, and NU0219142.

In further embodiments, the markers used to follow the presence of any of these QTL are selected from the group consisting of: NU0219671, NU0243432, NU0219672, NU0219774, NU0220446, NU0218512, NU0243542, NU0219676, NU0220613, NU0244254, NU0220202, and NU0218915. In other embodiments the markers used to follow the presence of any of these QTL are selected from the group consisting of: NU0220114, NU0219125, NU0220323, NU0244737, NU0218664, NU0243568, NU0219683, and NU0219142.

In yet other embodiments, the markers used to follow the presence of any of these QTL are selected from the group consisting of: NU0219671, NU0221090, NU0218604, NU0218684, NU0218148, NU0243432, NU0243324, NU0219095, NU0218257, NU0219354, NU0219672, NU0243607, NU0219118, NU0220372, NU0219774, NU0219889, NU0244419, NU0244478, NU0220446, NU0219650, NU0244718, NU0218943, NU0218512, NU0219136, NU0218860, NU0220597, NU0219475, NU0243542, NU0220825, NU0219448, NU0243629, NU0218829, NU0218923, NU0243807, NU0244022, NU0218871, NU0218901, NU0220173, NU0220684, NU0218887, NU0219803, NU0219004, NU0219642, NU0219025, NU0218757, NU0219015, NU0219386, NU0219676, NU0243281, NU0243478, NU0219177, NU0219316, NU0219426, NU0220839, NU0244508, NU0244665, NU0218187, NU0218513, NU0221036, NU0243535, NU0220613, NU0218306, NU0218509, NU0219086, NU0220451, NU0244507, NU0219425, NU0244254, NU0220942, NU0218848, NU0244041, NU0220202, NU0220577, and NU0218915.

In still yet other embodiments, the markers used to follow the presence of any of these QTL are selected from the group consisting of: NU0220114, NU0219003, NU0219125, NU0220581, NU0220762, NU0220116, NU0220849, NU0218843, NU0220323, NU0220985, NU0244737, NU0219214, NU0218908, NU0244415, NU0220766, NU0243268, NU0218664, NU0219506, NU0220650, NU0219176, NU0219728, NU0244427, NU0219075, NU0243568, NU0220301, NU0243578, NU0218206, NU0218955, NU0219589, NU0221079, NU0219683, NU0219740, NU0218191, NU0219782, and NU0219142.

In still further embodiments, the invention provides a method comprising obtaining a progeny plant that comprises a(n) allele(s) specifying increased Brix by identifying one or more genetic markers genetically linked to a high Brix melon QTL. Identifying the genetic markers may comprise a phenotypic, a genetic, or a biochemical test, and may include screening a parent and/or progeny plant for the presence of one or more of the alleles described herein, including, for example, one or more alleles of markers on melon linkage group 4, such as markers NU0219671, NU0243432, NU0219672, NU0219774, NU0220446, NU0218512, NU0243542, NU0219676, NU0220613, NU0244254, NU0220202, and NU0218915, among others. In some embodiments, screening for an allele of a marker linked within 10 cM of any of these above listed markers is also contemplated.

In one embodiment, screening for the presence of one or more alleles of a marker on melon linkage group 10 is contemplated, such as a marker selected from the group consisting of NU0220114, NU0219125, NU0220323, NU0244737, NU0218664, NU0243568, NU0219683, and NU0219142, among others. In some embodiments, screening for an allele of a marker linked within 10 cM of any of these above listed markers is also contemplated.

Screening for the presence of alleles of two or more genetic markers on linkage group 4 or linkage group 10 may also be carried our in accordance with the invention. Screening for the presence of one or more alleles of a marker on linkage group 4 and one or more alleles of a marker on linkage group 10 is contemplated in accordance with the invention. Further, selecting a progeny melon plant based on the presence of one or more alleles of such above-listed markers, or other marker(s) linked within 10 cM of any of the above listed markers, is also contemplated.

In certain embodiments, a method of the invention comprises identifying a *Cucumis melo* plant comprising a QTL introgression on LG4 mapping between, and including one or more of, markers NU0219671, NU0243432, NU0219672, NU0219774, NU0220446, NU0218512, NU0243542, NU0219676, NU0220613, NU0244254, NU0220202, and NU0218915, wherein the introgression confers elevated levels of Brix. In some embodiments a method of the invention comprises identifying a *Cucumis melo* plant comprising a QTL introgression on LG10 mapping between, and including one or more of, markers NU0220114, NU0219125, NU0220323, NU0244737, NU0218664, NU0243568, NU0219683, and NU0219142, wherein the introgression confers elevated levels of Brix. In other embodiments, the method may comprise screening for an allele found in the disclosed genetic interval of LG4 and for an allele found in the disclosed genetic interval of LG 10. In particular embodiments, the method comprises identifying a *Cucumis melo* plant comprising a high Brix QTL on melon LG4 and/or LG10. The method may also comprise crossing such a melon plant with another plant, and may further comprise identifying a progeny plant of any generation thereof that comprises a high Brix QTL as disclosed herein.

The invention therefore allows efficient screening for, and identification of, *Cucumis melo* plants and their progeny that comprise QTL conferring elevated Brix. This allows introduction of the high Brix QTL into any other genetic background capable of being bred with *Cucumis melo*.

The definition of these QTL allows the use of specific molecular markers, such as those disclosed herein, in a plant breeding program to introgress the elevated Brix into various agronomically acceptable *Cucumis melo* lines. Marker-assisted introgression involves the transfer of a chromosomal region, defined by one or more markers, from one germplasm to a second germplasm. An initial step in that process is the localization of the trait by gene mapping which is the process of determining the position of a gene relative to other genes and genetic markers through linkage analysis. The basic principle for linkage mapping is that the closer together two genes are on the chromosome, the more likely they are to be inherited together. Briefly, a cross is made between two genetically compatible but divergent parents relative to a trait under study (e.g. Brix content). Genetic markers may then be used to follow the segregation of traits under study in the progeny from the cross, often termed a "mapping population." The current invention allows introgression of QTL conferring elevated Brix content. In certain embodiments of the invention, the process for producing *Cucumis melo* plants with increased Brix comprises introgressing at least one chromosomal locus mapping to linkage group 4 or linkage group 10 of *C. melo* a *Cucumis melo* plant having relative high Brix content into a genetic background initially having lower relative Brix content. In specific embodiments, the chromosomal locus comprises a locus conferring high Brix that is found at linkage group 4 or linkage group 10 of line BEST.

Introgression of a particular DNA element or set of elements into a plant genotype is defined as the result of the process of backcross conversion. A plant genotype into which a DNA sequence has been introgressed may be referred to as a backcross converted genotype, line, or variety. Such genotype, line, or variety may be an inbred or a hybrid genotype, line, or variety. Similarly a plant genotype lacking said desired DNA sequence may be referred to as an unconverted genotype, line, or variety. During breeding, the genetic markers linked to an enhanced Brix content QTL may be used to assist in breeding for the purpose of producing *Cucumis melo* plants with increased Brix content. A skilled worker would understand that the introgression may be monitored by phenotypic assays, such as of Brix content, and/or by monitoring and breeding for the presence of molecular markers as described herein (i.e. marker assisted selection).

Localization of such markers to specific genomic regions or contigs further allows for use of associated sequences in breeding, to develop additional linked genetic markers, as well as to identify the mechanism for resistance at more precise genetic and biochemical levels. It will be understood to those of skill in the art that other markers or probes which more closely map the chromosomal regions as identified herein could be employed to identify plants comprising a desired QTL for Brix content. Linkage blocks of various sizes could be transferred within the scope of this invention as long as the chromosomal region enhances Brix content. Accordingly, it is emphasized that the present invention may be practiced using any informative molecular markers which genetically map in similar regions, provided that the markers are polymorphic between the parents.

Earliness is an important agronomic trait, as it allows growers to bring the harvest to market sooner and reduces the risks of crop loss. For example, many growing areas have an off-season with weather conditions that are detrimental to agriculture, such as cold, rain, or reduced sunlight. By growing an early maturing hybrid, a farmer could reduce the risk that his crop will not have been harvested prior to the onset of these conditions. Additionally, in regions where back to back crop cycles are possible, an early harvest will allow a second planting to fit more readily within ideal growing conditions. Also, the first fruits to market in a growing season can often fetch a premium price not available when the market is saturated shortly thereafter. Further, disease pressures often build up throughout a growing season and an early harvest will avoid the more severe disease pressures that occur late in the season or allow harvest from a field before disease symptoms fully develop and affect marketable yield from a crop.

Early development of fruit quality can also be exploited to reduce the number of field trips required to complete the harvest. In melons, the primary quality attribute used to determine acceptability and grade is Brix, or total soluble solids. For example, a Brix value of 9 is highly desirable for import to markets in the United States. For successful marketability, a grower cannot harvest fruit until each reaches acceptable quality levels, meaning that daily, or even twice-daily harvest passes may be needed to get maximum yield without compromising quality. In contrast, if the variety reaches good quality five to seven days earlier, the grower could wait to start harvesting the first set fruit and could make fewer passes through the field to complete the harvest while maintaining fruit quality. As shown in Example 6 and FIGS. 6-7, the high Brix QTL of linkage group 4 surprisingly allows for earlier accumulation of Brix to a desired level.

Flesh color is another hallmark of fruit quality which generally develops late in the maturation process. Further, it is known from consumer studies conducted in melons that consumers associate more vivid color with greater degrees of ripeness. The presence of the Brix QTL of linkage group 4, as found for instance in line Q4:B and as discussed in Example 6, allows for development of approximately mature orange flesh color earlier than expected, for instance at around 28 DPA. Further, Q4:B fruits have a deeper orange color at slip, thus the color of Q4:B at 28 DPA is predicted to be more ripe in appearance than that of, for instance, sister line Q4:1046 (lacking the sequences such as the Brix QTL on linkage group 4) at 37 DPA. It is especially surprising that the Q4:B line would exhibit a deeper orange color at maturity, given that the trait source 'Best' is a white-fleshed melon. However this appears to be a desirable linkage of the association of deeper color with early-maturing fruit.

The term "Brix" ("° Bx") is used here to quantify the mass ratio of dissolved solids, such as sucrose, to water in a liquid and is given in units of degrees ("°"). More specifically, a measurement of the Brix level of a melon fruit may be made according to methods well known in the art, for instance by use of a saccharimeter or refractometer (e.g. Atago pocket refractometer PAL-1; Atago USA, Inc., Bellevue, Wash.). For instance, a measurement of 10° Bx corresponds to about 7-8 grams of dissolved solids including sucrose per 100 grams of liquid. In certain embodiments the Brix level of such melon fruit may be, for instance, at least 9, 9.5, or 10° Bx.

As used herein, a "female parent" refers to a *Cucumis melo* plant that is the recipient of pollen from a male donor line, which pollen successfully pollinates an egg. A female parent can be any *Cucumis melo* plant that is the recipient of pollen. Such female parents can be male sterile, for example, because of genic male sterility, cytoplasmic male sterility, or because they have been subject to manual emasculation of the stamens. Genic or cytoplasmic male sterility can be manifested in different manners, such as sterile pollen, malformed or stamenless flowers, positional sterility, and functional sterility.

As used herein, "cytoplasmic male sterility" refers to plants that are not usually capable of breeding from self-pollination, but are capable of breeding from cross-pollination.

As used herein, "linkage" is a phenomenon wherein alleles on the same chromosome tend to segregate together more often than expected by chance if their transmission was independent.

As used herein, a "marker" is an indicator for the presence of at least one phenotype, genotype, or polymorphism. Markers include, but are not limited to, single nucleotide polymorphisms (SNPs), cleavable amplified polymorphic sequences (CAPS), amplified fragment length polymorphisms (AFLPs), restriction fragment length polymorphisms (RFLPs), simple sequence repeats (SSRs), insertion(s)/deletion(s) ("INDEL"(s)), inter-simple sequence repeats (ISSR), and random amplified polymorphic DNA (RAPD) sequences. DNA sequencing, e.g. of chromosomal DNA, may also be employed to determine the allele present at a given marker of interest. A marker is preferably inherited in codominant fashion (both alleles at a locus in a diploid heterozygote are readily detectable), with no environmental variance component, i.e., heritability of 1. A "nucleic acid marker" as used herein means a nucleic acid molecule that is capable of being a marker for detecting a polymorphism. Stringent conditions for hybridization of a nucleic acid probe or primer to a marker sequence or a sequence flanking a marker sequence refers, for instance, to nucleic acid hybridization conditions of 1×SSC and 65° C. As used herein, "marker assay" means a method for detecting a polymorphism at a particular locus using a particular method, e.g. measurement of at least one phenotype (such as a visually detectable trait, including disease resistance), restriction fragment length polymorphism (RFLP), single base extension, electrophoresis, sequence alignment, allelic specific oligonucleotide hybridization (ASO), random amplified polymorphic DNA (RAPD), microarray-based technologies, PCR-based technologies, and nucleic acid sequencing technologies, etc.

Desirable *Cucumis melo* plant traits, e.g. as displayed by agronomically elite lines or cultivars, and that may be independently selected include, but are not limited to: plant vigor, fruit flesh color, time to maturity, adaptation to field growth, adaptation to greenhouse growth, and resistance to one or more diseases or disease causing organisms.

Breeding of Melon Lines Displaying Elevated Levels of Brix

One aspect of the current invention concerns methods for crossing a *Cucumis melo* line comprising a QTL conferring elevated levels of Brix as described herein with itself or a second plant and the seeds and plants produced by such methods. These methods can be used for production and propagation of cultivated *Cucumis melo* lines and hybrids displaying elevated levels of Brix without agronomically undesirable traits that have previously been associated with the elevated Brix traits.

In accordance with the invention, novel varieties may be created by crossing elevated Brix QTL-containing lines followed by generations of selection as desired and inbreeding for development of uniform lines. New varieties may also be created by crossing with any second plant. In selecting such a second plant to cross for the purpose of developing novel lines, it may be desired to choose those plants which either themselves exhibit one or more selected desirable characteristics or which exhibit the desired characteristic(s) when in hybrid combination. Once initial crosses have been made, inbreeding and selection are subsequently used to produce new varieties. For development of a uniform line, often five or more generations of selfing and selection are typical.

Uniform lines of new varieties may also be developed by way of doubled-haploids. This technique allows the creation of true breeding lines without the need for multiple generations of selfing and selection. In this manner true breeding lines can be produced in as little as one generation. Haploid embryos may be produced from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with a plant of the present invention and progeny thereof to achieve a homozygous line.

Backcrossing can also be used to improve an inbred plant. Backcrossing transfers a specific desirable trait, such as elevated levels of Brix, from one inbred or non-inbred source to an inbred that lacks that trait. This can be accomplished, for example, by first crossing a superior inbred (recurrent parent) to a donor source (non-recurrent parent), which carries the appropriate locus or loci for the trait in question. The progeny of this cross are then mated back to the superior recurrent parent followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred. In this manner the recombined alleles provided by the invention may be introgressed into any *Cucumis melo* genotype.

Similarly, development of *Cucumis melo* varieties with improved traits by incorporation of alleles from a donor plant into an elite plant cultivar background can be accomplished efficiently using a method of Advanced Backcross QTL (AB-QTL) analysis (Tanksley and Nelson, 1996), followed by fine mapping analysis. Advanced backcross QTL analysis is a breeding strategy that allows the simultaneous identification of potentially useful alleles from donor germplasm and incorporation of those alleles into elite breeding material, using marker assisted selection. AB-QTL analysis is accomplished through the generation of a wild× elite hybrid, followed by a series of backcrosses to the elite parent, coupled with molecular marker and phenotypic selections. Backcross populations are subjected to QTL analysis for desirable traits, identifying genomic regions containing useful donor alleles that are introgressed into an elite cultivar genetic background, creating near isogenic lines (NILs). Finally, the NILs and the elite parent controls are evaluated for traits in replicated field trials (Bernacchi et al., 1998). In addition to AB-QTL analysis, subsequent fine-mapping analysis is often used to pinpoint the alleles influencing the trait of interest and eliminate linkage to undesirable alleles. This is accomplished by additional backcrosses, generating subNILs with reduced overlapping introgressions, that are further characterized by QTL analysis and molecular markers to more precisely define the introgression segments contributing to desired traits.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

*Cucumis melo* varieties can also be developed from more than two parents. The technique, known as modified backcrossing, uses different recurrent parents during backcrossing. Modified backcrossing may be used to replace the original recurrent parent with a variety having certain more desirable characteristics or multiple parents may be used to obtain different desirable characteristics from each.

Many single locus traits have been identified that are not regularly selected for in the development of a new inbred but that can be improved by backcrossing techniques. Single locus traits may or may not be transgenic; examples of these traits include, but are not limited to, herbicide resistance, resistance to bacterial, fungal, or viral disease, insect resistance, modified fatty acid or carbohydrate metabolism, and altered nutritional quality. These comprise genes generally inherited through the nucleus.

Direct selection may be applied where the single locus acts as a dominant trait. Selection of *Cucumis melo* plants for breeding is not necessarily dependent on the phenotype of a plant and instead can be based on genetic investigations. For example, one can utilize a suitable genetic marker which is closely genetically linked to a trait of interest. One such marker can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait of interest in a plant can also be useful for breeding purposes.

General procedures for marker assisted selection are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

Many useful traits are those which are introduced by genetic transformation techniques. The preparation of transgenes, e.g. by preparing recombinant constructs, and genetic transformation may therefore be used to directly insert a selected transgene into a plant of the invention or recombinant DNA sequences may, alternatively, subsequently be introduced into another genetic background by backcrossing. Methods for the transformation of plants that are well known to those of skill in the art and applicable to many crop species include, but are not limited to, electroporation, microprojectile bombardment, *Agrobacterium*-mediated transformation and direct DNA uptake by protoplasts.

Many hundreds if not thousands of different genes are known and could potentially be introduced into a *Cucumis melo* plant according to the invention. Non-limiting examples of particular genes and corresponding phenotypes one may choose to introduce into a *Cucumis melo* plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference in their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., 1991). The RNA could also be a catalytic RNA molecule (i.e., a ribozyme) engineered to cleave a desired endogenous mRNA product (see for example, Gibson and Shillito, 1997). Thus, any gene which produces a protein or mRNA which expresses a phenotype or morphology change of interest is useful for the practice of the present invention.

Definitions

In the description and tables herein, a number of terms are used. In order to provide a clear and consistent understanding of the specification and claims, the following definitions are provided:

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Brix: The content of total soluble solids, such as sugars and acids, in a *Cucumis melo* fruit, as measured by refractive index.

Cultivated *Cucumis melo*: *Cucumis melo* which is suitable for consumption and meets the requirements for commercial cultivation. In addition to the *Cucumis melo* plants themselves, and the parts thereof suitable for consumption, such as the fruit, the invention comprises parts or derivatives of the plant suitable for propagation. Examples of parts suitable for propagation are organ tissues, such as leaves, stems, roots, shoots and the like, protoplasts, somatic embryos, anthers, petioles, cells in culture and the like. Derivatives suitable for propagation are for instance seeds. The plants according to the invention can be cultivated or propagated in the conventional manner but also by means of tissue culture techniques from plant parts.

Crossing: The mating of two parent plants.

Cross-pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor or a chemical agent conferring male sterility.

Enzymes: Molecules which can act as catalysts in biological reactions.

$F_1$ Hybrid: The first generation progeny of the cross of two non-isogenic plants.

Genotype: The genetic constitution of a cell or organism. As used herein, "genotype" is the actual nucleic acid sequence at a locus in an individual plant. As used herein, "phenotype" means the detectable characteristics (e.g. Brix content) of a cell or organism which can be influenced by genotype.

Haploid: A cell or organism having one set of the two sets of chromosomes in a diploid.

Linkage: A phenomenon wherein alleles on the same chromosome tend to segregate together more often than expected by chance if their transmission was independent.

LOD score: The level of confidence in an estimate of linkage distance between two loci.

Marker: A readily detectable phenotype or genotype, preferably inherited in co-dominant fashion (both alleles at a locus in a diploid heterozygote are readily detectable), with no environmental variance component, i.e., heritability of 1.

Phenotype: The detectable characteristics of a cell or organism, which characteristics are the manifestation of gene expression.

Polymorphism means the presence of one or more variations of a nucleic acid sequence at one or more loci in a population of one or more individuals. The variation may comprise but is not limited to one or more base changes, the insertion of one or more nucleotides or the deletion of one or more nucleotides. A polymorphism may arise from random processes in nucleic acid replication, through mutagenesis, as a result of mobile genomic elements, from copy number variation and during the process of meiosis, such as unequal crossing over, genome duplication and chromosome breaks and fusions. The variation can be commonly found, or may exist at low frequency within a population, the former having greater utility in general plant breeding and the latter may be associated with rare but important phenotypic variation. Useful polymorphisms may include single nucleotide polymorphisms (SNPs), insertions or deletions in DNA sequence (Indels), simple sequence repeats of DNA sequence (SSRs) a restriction fragment length polymorphism, and a tag SNP. A genetic marker, a gene, a DNA-derived sequence, a haplotype, a RNA-derived sequence, a promoter, a 5' untranslated region of a gene, a 3' untranslated region of a gene, microRNA, siRNA, a QTL, a satellite marker, a transgene, mRNA, dsRNA, a transcriptional profile, and a methylation pattern may comprise polymorphisms. In addition, the presence, absence, or variation in copy number of the preceding may comprise a polymorphism.

Poor Plant Habit: Poor plant habit is characterized by increased plant vegetative growth. A *Cucumis melo* plant with poor plant habit exhibits increased vegetative growth in comparison with a cultivated *Cucumis melo* plant of desirable plant habit with more defined vegetative growth. *Cucumis melo* plant habit is rated on a scale of 1 to 9, where 1 is acceptable plant habit and 9 is poor plant habit.

Quantitative Trait Loci (QTL): Quantitative trait loci (QTL) refer to genetic loci that control to some degree numerically representable traits that are usually continuously distributed.

Recombination event: A meiotic crossing-over.

Regeneration: The development of a plant from tissue culture.

Self-pollination: The transfer of pollen from the anther to the stigma of the same plant.

Single Locus Converted (Conversion) Plant: Plants which are developed by a plant breeding technique called backcrossing, wherein essentially all of the morphological and physiological characteristics of a *Cucumis melo* variety are recovered in addition to the characteristics of the single locus transferred into the variety via the backcrossing technique and/or by genetic transformation.

Substantially Equivalent: A characteristic that, when compared, does not show a statistically significant difference (e.g., p=0.05) from the mean.

Tissue Culture: A composition comprising isolated cells of the same or a different type or a collection of such cells organized into parts of a plant.

Transgene: A genetic locus comprising a sequence which has been introduced into the genome of a *Cucumis melo* plant by transformation.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

EXAMPLES

Example 1

Development of Breeding Strategy

A breeding strategy was initiated to develop melon hybrids with improved fruit quality such as enhanced sweetness, and in particular increased Brix under adverse growing conditions. A Brix of 9 is often considered to be a minimum requirement for successful marketing of melons in US markets, and elsewhere. This threshold Brix level can be challenging to achieve in humid environments with relatively warm nights, such as conditions commonly encountered in certain melon growing regions of Central and South America and elsewhere. Thus melon fruit were screened for high Brix within elite inbreds from distinct melon market types, as these materials may contain beneficial alleles not found, or known to be present, in currently available WSH hybrids.

Potential sources of favorable alleles for Brix were identified by screening a panel of inbred lines for high Brix in Woodland, Calif. and Salama, Guatemala, both for their performance as inbreds per se and in test crosses to WSH and Eastern type melon lines. In particular, forty eight elite melon inbred lines chosen as having consistently high Brix were trialed. This assembled collection consisted primarily of Asian and inodorus lines, as these distinct market types were thought to contain beneficial genetics not commonly present in WSH types, and could therefore be used to improve fruit quality in unrelated market types.

Figure 2:
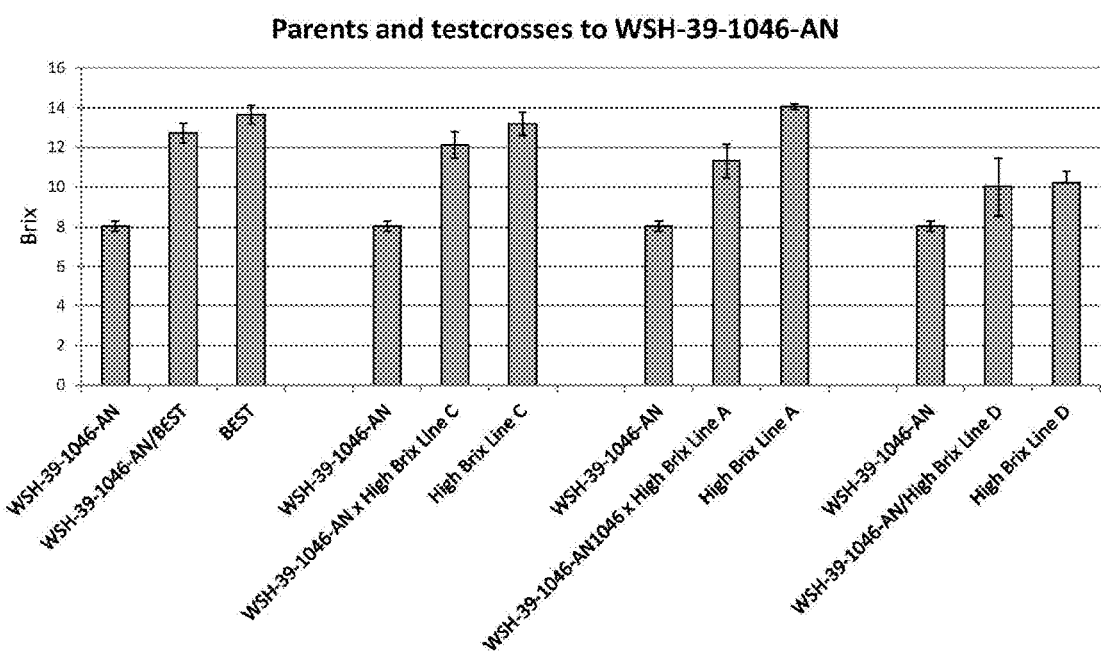
FIG. 2: Average Brix levels of the parents and test cross progeny of WSH 39-1046 AN with candidate Brix donor lines A, C, and D, with standard errors indicated.

These materials were grown and sampled in triplicate and evaluated for their soluble solids in comparison to a selection of WSH inbred lines in order to identify possible sources to achieve target Brix levels. Based on these data, a selection of high performing lines were test crossed to recipient lines WSH 39-1046 AN and EMM 39-1, and the parents and F1 progeny were assessed. Bulked fruit Brix was determined, and based on test cross results and line performance, a line designated "BEST" was thus identified as a high sugar inbred line that can contribute to improved Brix level and high soluble solids. FIG. 1 illustrates the performance of the five top lines from trials conducted at two locations, in comparison with the Brix level of parental and control lines (WSH 39-1046 AN, WSH 39-1370 AN, and EMM 39-1), and FIG. 2 illustrates data from certain test crosses to WSH 39-1046 AN.

Example 2

Recombinant Inbred Line (RIL) Development and Creation of Genetic Map

A recombinant inbred line (RIL) population was then developed using BEST, along with WSH 39-1046 as the low soluble solids parent. Individual RILs, propagated by single seed descent, were screened in three locations (Chile, Guatemala, and Woodland, Calif.). In addition to Brix measurements, fruit size and plant health data were collected to ensure that the uncovered QTL were not pleiotropic for undesirable traits, and to provide the highest quality phenotypic data possible; further in that disease ratings were strongly predictive of final Brix levels. After removing outliers using a pedigree based statistical model, the resulting data were used to map QTL for improved Brix.

Figure 3:
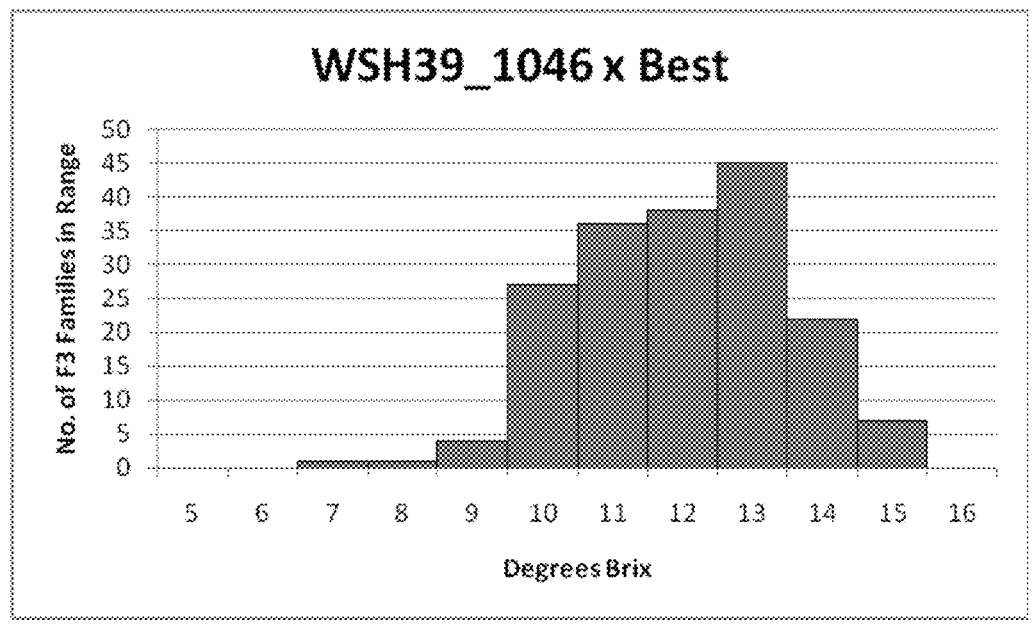
FIG. 3: Histogram of the average Brix levels of the F3 families derived from BEST, with the number of families in each bin on the y-axis, and bins labeled with the high end values.

179 RILs were then created by single seed descent from a single F1 plant for use in quantitative genetic studies. The F3 families established by this effort were grown in order to confirm segregation for Brix within the population and verify clear separation between the parents of the population. These data were obtained to confirm the utility of this population for mapping Brix QTL. BEST displayed an average Brix reading of 13.7 in this study, consistent with the averages of 13.7 and 15.8 observed in two previous trials. The observed Brix levels were also significantly higher than the low sugar parent, WSH 39-1046 AN, which had an average Brix of 8.6. A two tailed, heteroscedastic t-test showing a probability of significant difference of these values of 0.0068. FIG. 3 provides a histogram showing the distribution of average Brix levels in F3 families derived from line BEST. This result, combined with the broad, approximately normal distribution of the Brix data from the F3 families (FIG. 3), showed that the BEST×WSH 39-1046 AN RILs would be suitable to identify QTL from this source for subsequent breeding.

These RILs were genotyped at the F3 generation using SNP marker arrays, with a total of 1,238 polymorphic markers segregating in this population, of which 1,150 were placed on the genetic map. The completed map consisted of 13 linkage groups, ranging in size from 27.5 cM to 146.1 cM, and a small cluster of ten tightly linked markers totaling 1.5 cM. The average marker spacing was 1.8 cM, and the largest gap was 27.3 cM. A genetic map based on such melon SNPs segregating in the cross BEST×WSH 39-1046 AN is described in Table 2. This genetic map was compared to a separate melon genetic map, and all genetic results discussed below (linkage groups and genetic positions (cM)) refer to consensus map positions.

TABLE 2

Linkage groups and distribution of markers used to develop consensus melon genetic map.

| Linkage Group | Length (cM) | Number of Markers | Average distance between markers | Maximum distance between markers | Consensus LG |
|---|---|---|---|---|---|
| 1 | 111.0 | 96 | 1.2 | 13.4 | 3 |
| 2 | 77.6 | 85 | 0.9 | 13.0 | 2 |
| 3 | 34.3 | 31 | 1.1 | 8.1 | 12 |

TABLE 2-continued

Linkage groups and distribution of markers used to develop consensus melon genetic map.

| Linkage Group | Length (cM) | Number of Markers | Average distance between markers | Maximum distance between markers | Consensus LG |
|---|---|---|---|---|---|
| 4 | 132.2 | 139 | 1.0 | 10.4 | 4 |
| 5 | 118.5 | 105 | 1.1 | 9.0 | 11 |
| 6 | 27.5 | 36 | 0.8 | 5.0 | 12 |
| 7 | 119.1 | 114 | 1.1 | 27.3 | 7 |
| 8 | 112.6 | 100 | 1.1 | 11.0 | 9 |
| 9 | 84.5 | 103 | 0.8 | 9.0 | 8 |
| 10 | 105.1 | 80 | 1.3 | 22.3 | 1 |
| 11 | 146.1 | 120 | 1.2 | 12.7 | 6 |
| 12 | 106.6 | 65 | 1.7 | 14.8 | 5 |
| 13 | 80.7 | 65 | 1.3 | 18.0 | 10 |
| ** | 1.5 | 10 | 0.2 | 1.0 | 1 |
| Total | 1257.3 | 1,150 | 1.8 | 27.3 | — |

F4 progeny of the genotyped individuals were then tested in three trial locations for phenotypic analysis, including for Brix content. Each F4 family was planted in triplicate, and eight fruit were sampled per plot. Brix data were collected and data were analyzed in order to remove bias associated with disease gradients noted in some field locations, which impact overall plant vigor and thus affect Brix content as well.

Mixed model analysis revealed a significant effect of pedigree in each location (P<0.001), and control of error variance was acceptable, with the within location CVs between 9 and 15 percent. For each trial location, outlier analysis was performed within each pedigree using the deleted studentized residual for each line. Due to evident plant health/disease gradients at one location, a number of statistical models were considered to adjust the data for non-genetic nuisance effects. Based on the mean square error of prediction (MSEP), a model incorporating a plant health covariate, with nearest neighbor adjustments to correct for micro-environmental variation was chosen. This model gave an eight percent reduction in the MSEP, and successfully removed the gradient in disease symptoms and Brix values (data not shown). For data from a second location a model accounting for the plant health scores gave the best results as well. For data from a third location no further adjustments beyond the removal of outliers were possible due to the lack of covariate data and adequate field maps.

Example 3

QTL Analysis

Figure 4:
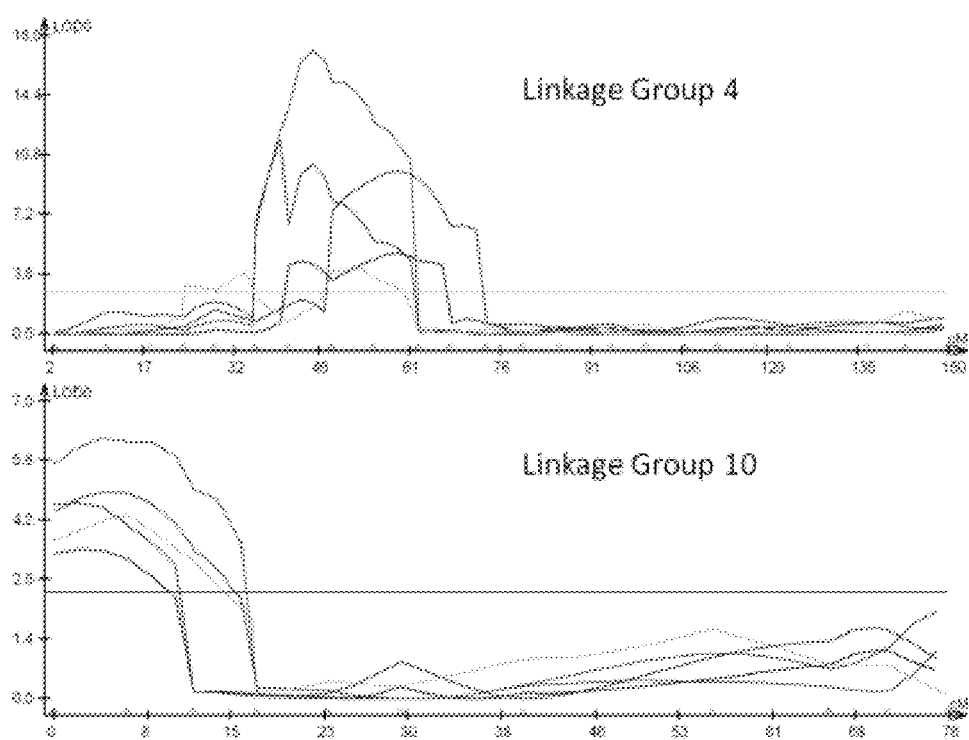
FIG. 4: Shown are the log of the odds (LOD) plots for linkage groups 4 and 10. The graphs represent raw and adjusted Brix values from three trial locations. The horizontal line indicates the permutation derived 95% confidence level for the presence of a QTL at any given locus. The cM units are the map positions on the melon consensus map.
Figure 5:
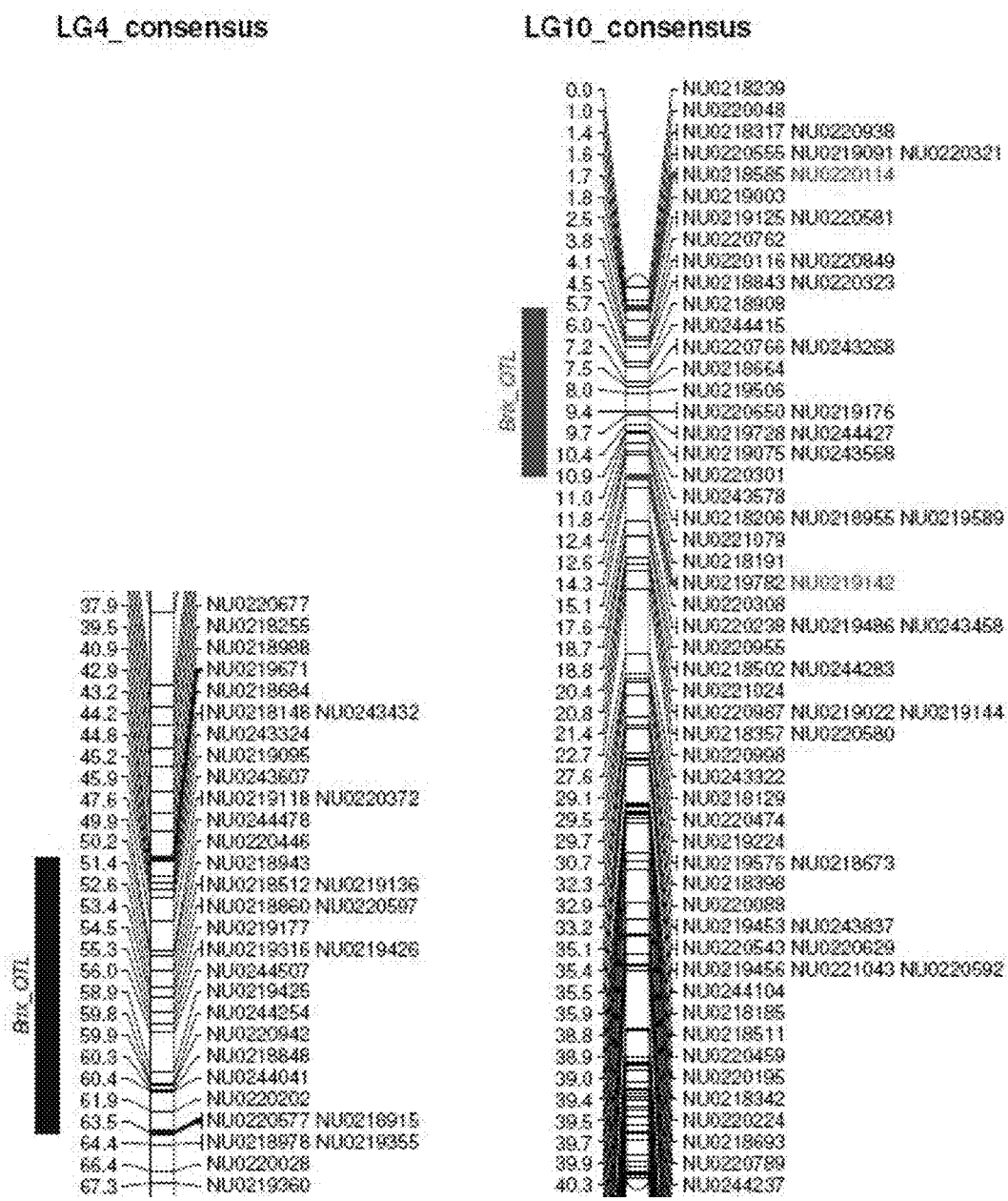
FIG. 5: The positions of the two Brix QTL on the *Cucumis melo* consensus genetic map are illustrated with thick bars indicating the 95% confidence interval. The QTL on linkage group 4 ("LG4") is bounded by markers NU0219671 (map position 42.9067 cM) and NU0218915 (map position 63.5466 cM), while the QTL on LG10 is bounded by markers NU0220114 (map position 1.670227 cM) and NU0219142 (map position 14.3257 cM). For clarity, only regions of interest are shown (from ~37.9 to ~67.3 cM on linkage group 4, and 0.0 to ~40.3 cM on LG10).

The least squares mean raw and adjusted Brix values for first two locations mentioned above, and the raw values from the third location, were then used for QTL analysis using the composite interval mapping algorithm implemented in Win-CartQTL (e.g. Wang et al., 2011). This analysis revealed two loci (QTL) in all three locations in both the raw and adjusted data which were derived from BEST and which contributed to elevated Brix. One identified QTL was located on linkage group four ("LG4") initially spanning approximately 25 cM. Another locus was found on linkage group ten ("LG10") spanning 15 cM, and the boundaries were subsequently refined further. FIG. 4 shows the output of the Composite Interval Mapping (CIM) analysis for LG4 and LG10. FIG. 5 shows a portion of the melon genetic map with marker density in the region of these loci, and indicates the 95% confidence interval for the placement of each locus using the adjusted Brix values from the first two locations, combined with raw values from the third growing location as discussed above. Table 3 provides key summary statistics for each locus, also calculated using the adjusted values where available. The 2-LOD score threshold interval for QTL of LG4 is bounded by markers NU0219671 (located at 42.0967 cM on consensus genetic map of FIG. 5) and NU0218915 (63.54661 cM). The 2-LOD score threshold interval for QTL of LG10 is bounded by markers NU0220114 (1.670227 cM) and NU0219142 (14.3257 cM).

TABLE 3

Summary of the QTL statistics. 99% confidence intervals, additive effect sizes, and $R^2$ values as calculated in QTL Cartographer. Positions of intervals are calculated from the above described mapping population.

| QTL | Trial Location | 2 LOD C.I. (cM) | Additive effect | $R^2$ | Marker # |
|---|---|---|---|---|---|
| CmBrix4_50 | 3 | 46-61 | 0.56 | .10 | 37 |
|  | 2 | 42-51 | 0.96 | .30 | 17 |
|  | 1 | 49-65 | 0.89 | .27 | 37 |
| CmBrix10_5 | 3 | 0-15 | 0.41 | .07 | 30 |
|  | 2 | 0-15 | 0.62 | .12 | 30 |
|  | 1 | 0-11 | 0.48 | .08 | 25 |

Thus the QTL analysis uncovered two loci derived from BEST which conferred increased Brix at each trial location. These QTL may be introgressed into parental inbred lines to provide improved fruit quality in melons, for instance as grown in Central and South America for export to the United States or elsewhere.

Example 4

QTL Validation: Brix and Fruit Size Phenotyping of Homozygous and Heterozygous Lines BC2-derived lines selected to carry homo- and heterozygous alleles at the QTL intervals of LG4 and LG10 were evaluated by collecting phenotypic data for the validation of the two melon Brix QTL, which were mapped in WSH 39-1046 AN×BEST segregating population. These QTL validation experiments consisted of 1 trial arranged in an RCBD design consisting of 5 replications, and included 5 controls per replication and a total of 100 plots, as well as 2 trials arranged in split-plot designs, where backcross families were the whole-plot factors and QTL genotypes were the subplots, consisting of 5 replications, and included 4 and 6 controls per replication and a total of 200 to 300 plots, respectively.

Five fruits were phenotyped per plot for Brix, flesh firmness, fruit size (length and width), and flesh color, as well as plant health, plot vigor, fruit set (number of fruits per plot) to validate the Brix QTL and evaluate linkage drag introduced by the QTL introgression. Brix, flesh firmness and color were phenotyped using handheld refractometer, penetrometer and colorimeter, respectively, while fruit size was evaluated as length and width of fruit cut along the stem and blossom end using digital caliper. RCBD and split plot designs were analyzed using linear and mixed models in SAS v 9.1 (SAS Institute, Cary, N.C., USA). All pairwise comparisons and specific within and across backcross family QTL genotype comparisons were tested. In addition, the additive and dominance effects were estimated for each backcross family. Table 4 provides exemplary results of this analysis. The least square means of QTL genotypes referred as 46/46, B/46 and H/46 correspond to introgressions homozygous for WSH 39-1046-AN, homozygous for BEST, and heterozygous for the QTL of interest shown in the second column, while the genomic interval for the second QTL is fixed for WSH 39-1046-AN. Additive and dominance effects, calculated using the least square means for each BC-derived family, are shown on the first row of each box, and p-values of these estimates are shown on the second row. Effects were declared significant at the $p<0.05$ threshold.

TABLE 4

Comparisons of Brix phenotypes (in °Brix) among BC-derived lines carrying homozygous and heterozygous introgressions of BEST and WSH 39-1046-AN for the QTL on LG4 and LG10 for one representative trial.

| Family | QTL | Brix lsmeans 46/46 | Brix lsmeans B/46 | Brix lsmeans H/46 | Additive effect/ p-value | Dominance effect/ p-value | Sugar lsmeans 46/46 | Sugar lsmeans B/46 | Sugar lsmeans H/46 | Additive effect/ p-value | Dominance effect/ p-value |
|---|---|---|---|---|---|---|---|---|---|---|---|
| 1 | LG 4 | 11.28 | 11.66 | 11.05 | 0.37 | 0.84 | 67.29 | 41.31 | 46.74 | −25.98 | 15.12 |
| 1 | LG 4 | | | | 0.37 | 0.26 | | | | <.0001 | 0.11 |
| 2 | LG 4 | 11.12 | 12.25 | 12.27 | 1.13 | −1.18 | 67.69 | 51.04 | 69.76 | −16.64 | −20.79 |
| 2 | LG 4 | | | | 0.009 | 0.09 | | | | 0.015 | 0.062 |
| 3 | LG 4 | 10.81 | 11.70 | 12.38 | 0.89 | −2.24 | 60.49 | 32.92 | 49.47 | −27.57 | −5.52 |
| 3 | LG 4 | | | | 0.011 | 0.0006 | | | | <.0001 | 0.53 |
| 4 | LG 4 | 11.15 | 12.87 | 12.45 | 1.72 | −0.88 | 76.47 | 53.59 | 60.70 | −22.88 | 8.66 |
| 4 | LG 4 | | | | <.0001 | 0.08 | | | | <.0001 | 0.28 |
| 5 | LG 4 | 10.18 | 12.14 | 11.63 | 1.96 | −0.95 | 46.92 | 38.71 | 46.53 | −8.21 | −7.43 |
| 5 | LG 4 | | | | <.0001 | 0.19 | | | | 0.078 | 0.32 |
| 1 | LG 10 | 10.27 | 11.91 | 12.03 | 1.64 | −1.89 | 61.51 | 87.89 | 81.96 | 26.38 | −14.52 |
| 1 | LG 10 | | | | <.0001 | 0.003 | | | | 0.0014 | 0.282 |
| 2 | LG 10 | 10.34 | 12.73 | 12.08 | 2.38 | −1.08 | 51.20 | 94.17 | 79.17 | 42.98 | −12.97 |
| 2 | LG 10 | | | | <.0001 | 0.06 | | | | <.0001 | 0.232 |
| 3 | LG 10 | 10.36 | 10.40 | 9.20 | 0.04 | 2.37 | 49.73 | 48.42 | 49.05 | −1.32 | 0.06 |
| 3 | LG 10 | | | | 0.88 | <.0001 | | | | 0.76 | 0.99 |
| 4 | LG 10 | 10.65 | 11.48 | 11.50 | 0.83 | −0.88 | 60.05 | 80.30 | 72.39 | 20.25 | <4.44 |
| 4 | LG 10 | | | | 0.032 | 0.19 | | | | 0.002 | 0.68 |
| 5 | LG 10 | 11.13 | 11.82 | 11.48 | 0.70 | −0.01 | 73.24 | 78.35 | 79.82 | 5.11 | −8.05 |
| 5 | LG 10 | | | | 0.03 | 0.98 | | | | 0.42 | 0.47 |

Table 5 provides exemplary results of comparisons of fruit length and width phenotypes for the QTL on LG4 and LG10 for one of the trials.

TABLE 5

Comparisons of fruit length and width phenotypes (in mm) among BC-derived lines carrying homozygous and heterozygous introgressions of BEST and WSH 39-1046-AN for the QTL on LG4 and LG10.

| Family | QTL | Length lsmeans 46/46 | Length lsmeans B/46 | Length lsmeans H/46 | Additive effect/ p-value | Dominance effect/ p-value | Width lsmeans 46/46 | Width lsmeans B/46 | Width lsmeans H/46 | Additive effect/ p-value | Dominance effect/ p-value |
|---|---|---|---|---|---|---|---|---|---|---|---|
| 1 | LG 4 | 141.58 | 120.30 | 127.25 | −21.28 | 7.38 | 133.01 | 112.56 | 119.98 | −20.45 | 5.62 |
| 1 | LG 4 | | | | <.0001 | 0.31 | | | | <.0001 | 0.28 |
| 2 | LG 4 | 139.89 | 126.69 | 139.90 | −13.2 | −13.22 | 135.60 | 117.81 | 131.16 | −17.79 | −8.92 |
| 2 | LG 4 | | | | 0.0009 | 0.03 | | | | <.0001 | 0.10 |

TABLE 5-continued

Comparisons of fruit length and width phenotypes (in mm) among BC-derived
lines carrying homozygous and heterozygous introgressions of BEST
and WSH 39-1046-AN for the QTL on LG4 and LG10.

| Family | QTL | Length lsmeans 46/46 | Length lsmeans B/46 | Length lsmeans H/46 | Additive effect/ p-value | Dominance effect/ p-value | Width lsmeans 46/46 | Width lsmeans B/46 | Width lsmeans H/46 | Additive effect/ p-value | Dominance effect/ p-value |
|---|---|---|---|---|---|---|---|---|---|---|---|
| 3 | LG 4 | 134.72 | 112.45 | 125.04 | −22.27 | −2.92 | 132.73 | 106.92 | 117.59 | −25.82 | 4.46 |
| 3 | LG 4 | | | | <.0001 | 0.73 | | | | <.0001 | 0.42 |
| 4 | LG 4 | 147.55 | 127.42 | 130.98 | −20.13 | 13.01 | 139.86 | 118.12 | 127.13 | −21.74 | 3.73 |
| 4 | LG 4 | | | | <.0001 | 0.04 | | | | <.0001 | 0.44 |
| 5 | LG 4 | 133.25 | 122.27 | 128.55 | −10.98 | −1.59 | 123.05 | 107.55 | 116.24 | −15.5 | −1.87 |
| 5 | LG 4 | | | | 0.0109 | 0.82 | | | | <.0001 | 0.71 |

A significant increase in Brix was confirmed when the BEST allele was introgressed on LG4 (average 2a=1.79° Brix) in 2 of the 3 trials, as well as significant decrease in firmness (average 2a=0.82 kgf), fruit length (average 2a=14.18 mm), and width (average 2a=15.1 mm). The presence of the Brix QTL on LG10 (average 2a=1.16° Brix) was also confirmed. Significant differences in Brix were observed among different backcross lines in all trials.

To investigate the negative association between Brix and fruit size for the QTL on LG4, sugar content was calculated using assumptions on fruit shape, rind and cavity size (total fruit flesh volume equal to $[((4/3)*\pi*((Length-10)/2)* ((Width-10)/2)2)*0.82]/1000$ assuming fruit is an ellipsoid, rind thickness=5 mm, seed cavity=18% fruit volume, fruit density=1 g/cm$^3$) and the equation derived from historical data: [Brix=1.4*(% sugar)+0.6] ($R^2$=0.87 as shown from our previous data). The BEST introgression on LG4 was shown to lead to a significant decrease in the total sugar content per fruit (average 2a=17.46 g); therefore, the increase in Brix could be due to a decrease in fruit size. The negative association between the Brix QTL on LG4 and fruit size may thus be due to pleiotropy or close linkage with this trait. The Brix QTL on LG10 was also shown to increase sugar content significantly (average 2a=22.93 g).

To validate the Brix QTL on LG4 and LG10 in testcross combinations and confirm efficacy of the two QTL in broader germplasm another trial was conducted under commercial growing conditions during the fall of 2010. Testcrosses of BC2-derived lines carrying the introgressions of BEST or WSH 39-1046 AN at the QTL on LG4 and LG10 to 4 inbred testers (WSH-39-1066-AN, CHA-38-MONEY, WSH-39-1074-AN and ITA-39-4006-AN) were evaluated. The trial was arranged in a split-plot design with 6 replications and had a total of 96 plots. Five fruits per plot were phenotyped for Brix, firmness and fruit size (length and width). Due to earlier than expected maturation of the fruit, several plots had already passed the optimal maturity stage for Brix evaluation, and data was collected from 53% of the initially targeted number of fruits. However, results confirmed the effect of the QTL on LG4 in 3 of the 4 testcrosses (average 2aT=2.32° Brix), all apart from WSH-39-1074-AN. The effect of the LG4 QTL on fruit size was also confirmed. A decrease in length (average 2aT=−24.11 mm) and width (average 2aT=−23.11 mm) was found in testcrosses with all 4 testers.

To confirm the efficacy of QTL10 in different melon lines, two additional trials were conducted. The first trial had tester as the whole-plot factor (WSH-39-1066-AN, WSH-39-1074-AN, ITA-39-4006-AN and CHA-38-MONEY), presence/absence of the BEST QTL10 introgressions as the split-plot factor, and had a total of 8 entries with 15 replications. Five fruit were phenotyped from each 10-plant plot for Brix, firmness and fruit size (length/width). ANOVAs, least square means, mean separation groupings and comparisons were estimated using SAS with an appropriate mixed model for this split plot design.

Results of the first additional trial confirmed a significant increase in Brix due to the BEST introgression on QTL10 for three of the four testers, and therefore confirm efficacy of QTL10 in ITA, CHA and WSH-type melons (Table 6). No significant decrease in firmness was observed, and in the case of CHA-38-MONEY the BEST introgression on QTL10 led to significant increase in firmness. Significant increase in fruit length and width was observed for the three CHA and WSH testers, but not the ITA tester (Table 6).

The second trial was designed with tester as the whole-plot factor (20070817 (ITA), WSH-39-1070-MO, CHA-192-ONTARIO-AN, GAL-188-COR-MO) and presence/absence of the BEST QTL10 as well as QTL4 and QTL10 introgressions as the split-plot factor. The trial had a total of 12 entries with 15 replications. Phenotyping and data analysis was conducted as previously described.

Results confirmed a significant increase in Brix due to the BEST introgression on QTL10 in 20070817 and GAL-188-COR-MO, and significant increase due to the BEST introgressions at both QTL10 and QTL4 in 20070817, CHA-192-ONTARIO-AN and WSH-39-1070-AN (Table 7).

No significant decrease in firmness was observed, and in the case of GAL-188-COR-MO the BEST introgression on QTL10 and QTL4/QTL10 led to significant increase in firmness. GAL-188-COR-MO and 20070817 had significantly lower fruit length and width only in testcrosses with lines carrying both BEST QTL introgressions (Table 7). Significant increase in fruit length and width due to the BEST introgression on QTL10 was only observed for the GAL tester, but not for CHA and WSH as in the previous experiment.

From the two experiments, as well as previous data on testcrosses with QTL4, it can be concluded that the efficacy of the Brix QTL has been confirmed for several tested melon lines (e.g. ITA, CHA, WSH and GAL for QTL10; and ITA, CHA and WSH for QTL4). QTL4 led to a decrease in fruit size (length and width) across tested melon lines (WSH, ITA, GAL and CHA). Similarly, QTL10 led to increase in firmness (in CHA and GAL) and fruit size (in CHA, WSH, and GAL).

TABLE 6

Least square means estimates (LSM), lower and upper 95% confidence intervals of these estimates (L_ and U_95% CI), and mean separation groupings (MSG) for all entries and traits tested.

| Tester | QTL LG10 | Brix | | | | Firmness | | | |
|---|---|---|---|---|---|---|---|---|---|
| | | LSM | L_95% CI | U_95% CI | MSG | LSM | L_95% CI | U_95% CI | MSG |
| ITA-39-4006-AN | 1046 | 12.02 | 11.33 | 12.71 | B | 7.3 | 6.62 | 7.97 | A |
| ITA-39-4006-AN | BEST | 12.95 | 12.27 | 13.64 | A | 7.53 | 6.86 | 8.2 | A |
| CHA-38-MONE | 1046 | 11.26 | 10.57 | 11.95 | BC | 4.87 | 4.2 | 5.55 | D |
| CHA-38-MONEY | BEST | 13.21 | 12.52 | 13.90 | A | 7.79 | 7.12 | 8.47 | A |
| WSH-39-1066 AN | 1046 | 9.56 | 8.86 | 10.27 | D | 6.11 | 5.41 | 6.80 | C |
| WSH-39-1066 AN | BEST | 10.96 | 10.27 | 11.65 | C | 6.22 | 5.55 | 6.90 | BC |
| WSH-39-1074 AN | 1046 | 10.74 | 10.05 | 11.43 | C | 7.16 | 6.48 | 7.83 | A |
| WSH-39-1074 AN | BEST | 10.98 | 10.29 | 11.66 | C | 7.07 | 6.40 | 7.74 | AB |

| Tester | Fruit Length | | | | Fruit Width | | | |
|---|---|---|---|---|---|---|---|---|
| | LSM | L_95% CI | U_95% CI | MSG | LSM | L_95% CI | U_95% CI | MSG |
| ITA-39-4006-AN | 160.97 | 157.06 | 164.87 | BCD | 141.04 | 138.59 | 143.48 | D |
| ITA-39-4006-AN | 155.54 | 151.77 | 159.32 | D | 142.19 | 139.83 | 144.55 | CD |
| CHA-38-MONE | 156.04 | 152.27 | 159.82 | D | 128.54 | 126.18 | 130.90 | F |
| CHA-38-MONEY | 164.10 | 160.32 | 167.87 | BC | 133.90 | 131.54 | 136.26 | E |
| WSH-39-1066 AN | 158.81 | 154.91 | 162.72 | CD | 145.55 | 143.11 | 148.00 | C |
| WSH-39-1066 AN | 164.89 | 161.11 | 168.67 | B | 154.80 | 152.44 | 157.16 | AB |
| WSH-39-1074 AN | 161.94 | 158.16 | 165.72 | BC | 151.54 | 149.18 | 153.90 | B |
| WSH-39-1074 AN | 172.86 | 169.09 | 176.64 | A | 156.29 | 153.93 | 158.65 | A |

TABLE 7

Least square means estimates (LSM), lower and upper 95% confidence intervals of these estimates (L_ and U_95% CI), and mean separation groupings (MSG) for all entries and traits tested.

| Tester | QTL | Brix | | | | Firmness | | | |
|---|---|---|---|---|---|---|---|---|---|
| | | LSM | L_95% CI | U_95% CI | MSG | LSM | L_95% CI | U_95% CI | MSG |
| 20070817 | 1046:1046 | 10.6 | 9.8 | 11.4 | FG | 8.2 | 7.6 | 8.7 | A |
| | 1046:BEST | 11.9 | 11.1 | 12.7 | DE | 7.7 | 7.2 | 8.2 | AB |
| | BEST:BEST | 13.4 | 12.6 | 14.2 | B | 8.0 | 7.5 | 8.6 | A |
| CHA-192-ONTARIO-AN | 1046:1046 | 13.0 | 12.2 | 13.8 | BC | 7.2 | 6.7 | 7.7 | BC |
| | 1046:BEST | 13.4 | 12.6 | 14.2 | B | 7.3 | 6.7 | 7.8 | BC |
| | BEST:BEST | 14.7 | 13.9 | 15.5 | A | 6.8 | 6.3 | 7.4 | C |
| GAL-188-CORMO | 1046:1046 | 12.1 | 11.2 | 12.9 | CD | 4.7 | 4.2 | 5.3 | E |
| | 1046:BEST | 13.2 | 12.4 | 14.0 | B | 7.2 | 6.6 | 7.7 | BC |
| | BEST:BEST | 13.8 | 13.0 | 14.6 | AB | 6.7 | 6.2 | 7.2 | C |

TABLE 7-continued

Least square means estimates (LSM), lower and upper 95% confidence intervals of these estimates (L_ and U_95% CI), and mean separation groupings (MSG) for all entries and traits tested.

| | | | | | | | | | |
|---|---|---|---|---|---|---|---|---|---|
| WSH-39-1070-AN | 1046:1046 | 9.7 | 8.8 | 10.6 | FG | 5.6 | 5.1 | 6.2 | D |
| | BEST:1046 | 9.6 | 8.8 | 10.4 | G | 5.7 | 5.2 | 6.2 | D |
| | BEST:BEST | 10.7 | 9.9 | 11.5 | EF | 5.4 | 4.9 | 5.9 | DE |

| | Fruit length | | | | Fruit width | | | |
|---|---|---|---|---|---|---|---|---|
| Tester | LSM | L_95% CI | U_95% CI | MSG | LSM | L_95% CI | U_95% CI | MSG |
| 20070817 | 195.3 | 191.0 | 199.7 | A | 160.2 | 157.4 | 163.0 | A |
| | 194.8 | 190.5 | 199.1 | A | 160.1 | 157.3 | 162.9 | A |
| | 176.3 | 172.0 | 180.6 | B | 149.7 | 146.9 | 152.5 | BCD |
| CHA-192-ONTARIO-AN | 126.9 | 122.6 | 131.2 | D | 129.0 | 126.2 | 131.8 | E |
| | 125.7 | 121.4 | 130.0 | D | 130.3 | 127.5 | 133.1 | E |
| | 127.4 | 123.1 | 131.7 | D | 128.4 | 125.6 | 131.2 | E |
| GAL-188-CORMO | 181.5 | 177.0 | 186.0 | B | 152.9 | 150.0 | 155.8 | B |
| | 190.7 | 186.3 | 195.0 | A | 161.1 | 158.3 | 163.9 | A |
| | 177.6 | 173.3 | 181.9 | B | 148.9 | 146.1 | 151.7 | CD |
| WSH-39-1070-AN | 160.7 | 155.9 | 165.6 | C | 151.8 | 148.7 | 154.9 | BC |
| | 155.9 | 151.4 | 160.3 | C | 148.7 | 145.8 | 151.6 | CD |
| | 154.6 | 150.2 | 158.9 | C | 147.7 | 144.9 | 150.5 | D |

No significant decrease in firmness was observed, and in the case of GAL-188-COR-MO the BEST introgression on QTL10 and QTL4/QTL10 led to significant increase in firmness. GAL-188-COR-MO and 20070817 had significantly lower fruit length and width only in testcrosses with lines carrying both BEST QTL introgressions (Table 5). Significant increase in fruit length and width due to the BEST introgression on QTL10 was only observed for the GAL tester, but not for CHA and WSH as in the previous experiment. Thus, significant increase in Brix due to the BEST homozygous introgression in BC2-derived lines for the QTL on LG4 (average 2a=1.79° Brix) and LG10 (average 2a=1.16° Brix) was demonstrated.

Example 5

Introgression of Brix QTL of LG4 in a Monoecious Melon Line

The Brix QTL from LG4 (i.e. "QTL04") conferred from the donor line BEST was associated with significant decrease in melon fruit size (average 2a=−14.2 mm fruit length; average 2a=−15.1 mm fruit width) and firmness (average 2a=−0.82 kgf). According to breeding observations monoecious melon lines manifest a greater degree of dominance for fruit size and shape. Therefore, testcrosses of 3 monoecious lines from selected melon types WSH-42-120-MO, HAR-173-10-4013-MO, and 20070817 (ITA) were performed with selected BC2F3 lines carrying or lacking the BEST introgression on LG4 to assess the decrease in fruit size in monoecious background, and explore further the possibility of deployment of the Brix QTL on LG4 in monoecious lines.

A split plot trial was designed with tester as the whole-plot factor (WSH-42-120-MO, HAR-173-10-4013-MO, 20070817) and presence/absence of the BEST QTL4 introgression as the split-plot factor. The trial had a total of 6 entries with 10 replications. Five fruit were phenotyped from each 10-plant plot for Brix, firmness and fruit size (length/width). ANOVAs, least square means, mean separation groupings and comparisons were estimated using SAS with an appropriate mixed model for this split plot design.

Results showed that all testcrosses derived from a cross of a monoecious line to a line carrying the homozygous BEST introgression on LG4 had significantly higher Brix (average 2aT=2.03° Brix), lower firmness (2 of 3) and lower fruit length (average 2aT=−8.44 mm) and width (average 2aT=−5.35 mm) (Tables 8 and 9). A similar trial was then conducted under commercial growing conditions, with WSH-39-1066-AN, CHA-38-MONEY, WSH-39-1074-AN and ITA-39-4006-AN as testers, and the testcross effect estimated for Brix was comparable with this experiment (average 2aT=2.32° Brix), although testcross effects implied a more drastic decrease in fruit length and width (length: average 2aT=−24.11 mm; width: average 2aT=−23.11 mm). The estimated testcross effects for fruit length and width in this experiment demonstrate a moderate decrease in fruit size, which implies that monoecious lines can "hide" the fruit size phenotype. Thus an exemplary breeding cross would be to introgress the QTL of LG4 into an andromonoecious male to be crossed with a monoecious female with large fruit size.

TABLE 8

Least square means estimates ("LSM"), lower and upper 95% confidence intervals of those estimates ("L_ and U_95% CI"), and mean separation groupings ("MSG") for tested entries and traits.

| Trait | Brix | | | | Firmness | | | |
|---|---|---|---|---|---|---|---|---|
| Entry ID | LSM | L_95% CI | U_95% CI | MSG | LSM | L_95% CI | U_95% CI | MSG |
| 20070817/QTL4:1046 | 11.6 | 11.1 | 12.2 | B | 8.4 | 7.4 | 9.5 | A |
| 20070817/QTL4:BEST | 13.2 | 12.7 | 13.8 | A | 6.7 | 5.7 | 7.8 | BC |

TABLE 8-continued

Least square means estimates ("LSM"), lower and upper 95% confidence intervals of those estimates ("L_ and U_95% CI"), and mean separation groupings ("MSG") for tested entries and traits.

| | | | | | | | | |
|---|---|---|---|---|---|---|---|---|
| HAR-173-10-4013-MO/QTL4:1046 | 9.5 | 8.9 | 10.0 | C | 8.0 | 7.0 | 8.9 | AB |
| HAR-173-10-4013-MO/QTL4:BEST | 12.9 | 12.4 | 13.5 | A | 7.9 | 6.9 | 8.8 | AB |
| WSH-42-120-MO/QTL4:1046 | 8.6 | 8.1 | 9.2 | D | 6.6 | 5.6 | 7.5 | B |
| WSH-42-120-MO/QTL4:BEST | 9.7 | 9.1 | 10.2 | C | 5.7 | 4.7 | 6.7 | C |

| Trait | Fruit width | | | | Fruit length | | | |
|---|---|---|---|---|---|---|---|---|
| Entry ID | LSM | L_95% CI | U_95% CI | MSG | LSM | L_95% CI | U_95% CI | MSG |
| 20070817/QTL4:1046 | 153.4 | 150.8 | 155.9 | C | 182.4 | 178.6 | 186.3 | A |
| 20070817/QTL4:BEST | 148.1 | 145.7 | 150.5 | D | 169.9 | 166.2 | 173.5 | C |
| HAR-173-10-4013-MO/QTL4:1046 | 147.8 | 145.4 | 150.2 | D | 168.7 | 165.1 | 172.4 | C |
| HAR-173-10-4013-MO/QTL4:BEST | 141.3 | 138.9 | 143.7 | E | 161.6 | 157.9 | 165.2 | D |
| WSH-42-120-MO/QTL4:1046 | 167.9 | 165.5 | 170.3 | A | 182.2 | 178.5 | 185.9 | A |
| WSH-42-120-MO/QTL4:BEST | 163.6 | 161.1 | 166.1 | B | 176.6 | 172.8 | 180.5 | |

TABLE 9

Comparisons of entries lacking and carrying the BEST introgression at QTL4 within tester (QTL4:1046-QTL4:BEST is shown as Delta), lower and upper 95% confidence intervals of this estimate and p-values for all testers and traits phenotyped.

| | Brix | | | | Firmness | | | | Fruit width | | | | Fruit length | | | |
|---|---|---|---|---|---|---|---|---|---|---|---|---|---|---|---|---|
| Trait Tester | Delta | P-value | Lower | Upper | Delta | P-value | Lower | Upper | Delta | P-value | Lower | Upper | Delta | P-value | Lower | Upper |
| 20070817 | −1.58 | 0.00 | −2.39 | −0.76 | 1.66 | 0.00 | 0.68 | 2.64 | 5.26 | 0.00 | 1.76 | 8.76 | 12.59 | 0.0.00 | 7.25 | 17.93 |
| HAR-173-10-4013-MO | −3.50 | 0.00 | −4.29 | −2.70 | 0.1 | 0.82 | −0.78 | 0.98 | 6.46 | 0.00 | 3.06 | 9.87 | 7.16 | 0.01 | 1.96 | 12.35 |
| WSH-42-120-MO | −1.02 | 0.02 | −1.83 | −0.21 | 0.92 | 0.05 | 0.00 | 1.85 | 4.34 | 0.02 | 0.84 | 7.84 | 5.58 | 0.04 | 0.23 | 10.92 |

Example 6

Introgression of Brix QTL of LG4 Confers Early Brix Accumulation

Figure 6:
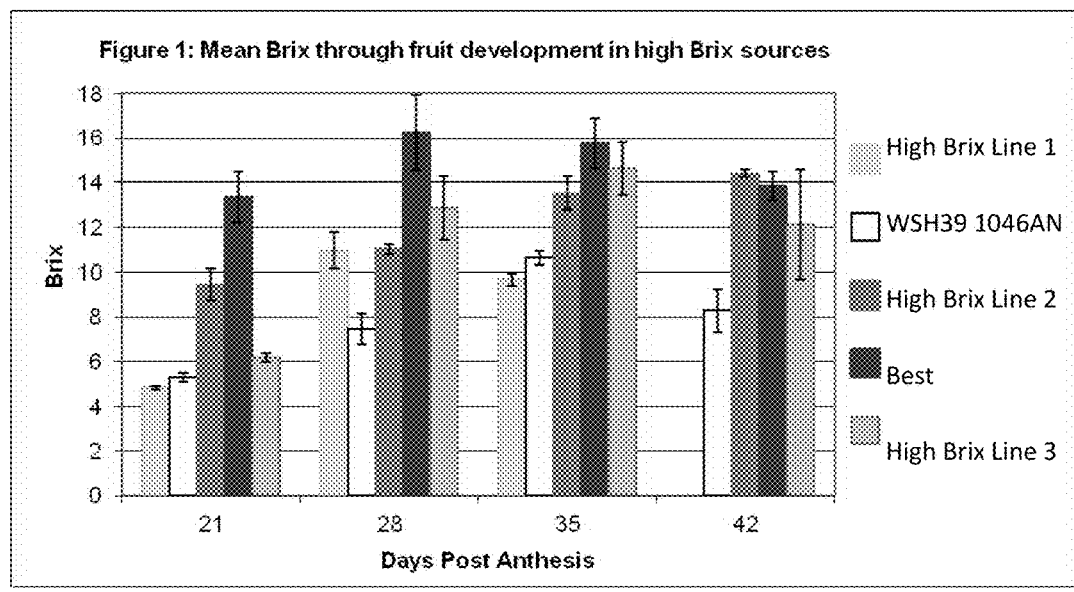
FIG. 6: Mean Brix through fruit development in high Brix sources. Data columns at each timepoint for Days Post Anthesis on the X axis are from left to right: High Brix Line 1, WSH39 1046AN, High Brix Line 2, Best, and High Brix Line 3. Note there is no data for High Brix Line 1 at 42 Days Post Anthesis.

During the screening of germplasm to identify sources for increased Brix levels, it was observed that one leading candidate, the line called 'Best' was surprisingly also noted for the early accumulation of Brix relative to physiological maturity (FIG. 6). As such, the strongest effect high Brix QTL (QTL04) was tested to determine whether this locus confers early Brix development.

A pair of sister BC2S1 lines were selected harboring the QTL with alternative allelic states at the QTL on LG4. The sister line with the QTL04 high Brix allele at the identified QTL on linkage group 4 is referred to as "Q4:B" and that with the recurrent parent allele at the identified QTL on linkage group 4 is referred to as "Q4:1046". These lines, along with the recurrent parent WSH 39-1046 AN and 'Best' were transplanted in large plots, with five replicates of each line, 30 plants per plot, and with three foot spacing between plants. Two individual female flowers were tagged at anthesis and allowed to pollinate using bees. Each plant was randomly selected to have one fruit harvested at each time point post anthesis beginning at 28 days post anthesis (DPA). The starting point of 28 DPA was chosen based on the expected physiological maturity for the recurrent parent being approximately 42 DPA.

Figure 7:
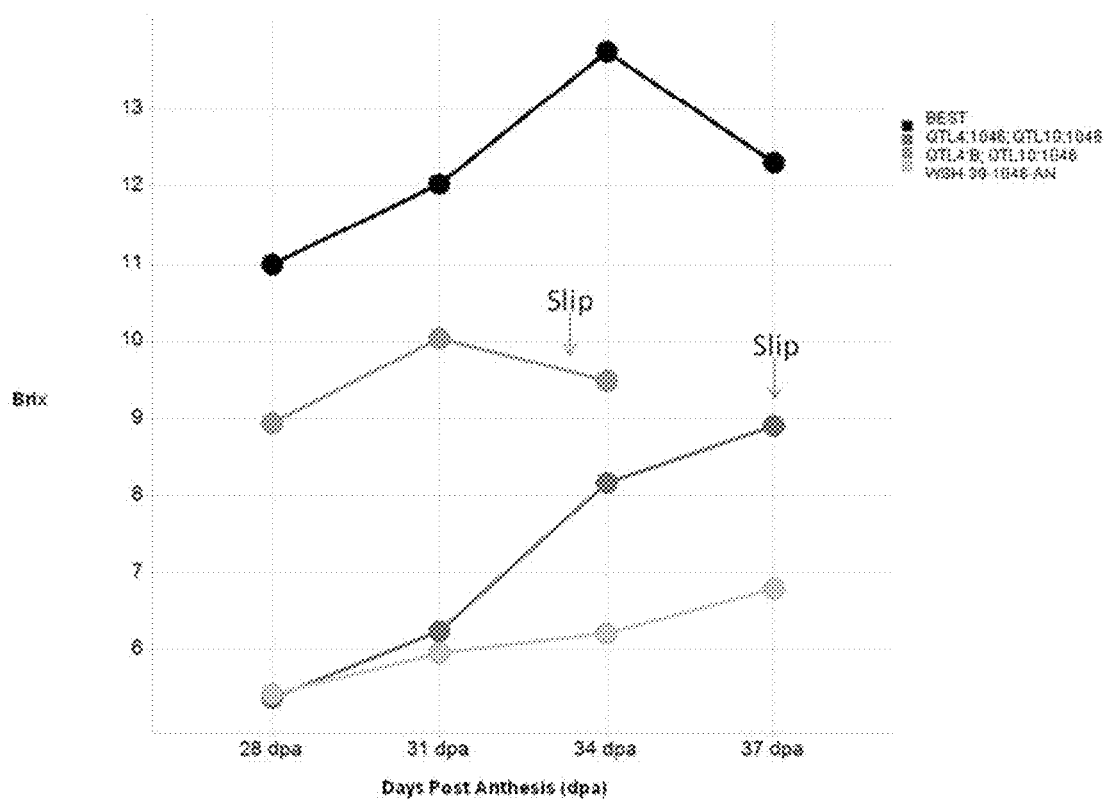
FIG. 7: LS mean values of Brix for each line and time point post anthesis. Y axis is LS means Brix and X axis is days post anthesis (dpa). 'Best' is shown in black, Q4:B in dark gray, Q4:1046 in medium gray, and WSH 39-1046 AN in light gray. The approximate date of slip is indicated by the arrows. Note that the process of slipping progresses from quarter slip through to full slip, with quarter slip representing commercial maturity. Since Q4:B was at full slip at 34 DPA we can infer that quarter slip would occur approximately 1 day earlier. Q4:1046 was at quarter slip at 37 DPA. WSH 39-1046 AN does not slip until approximately 42 DPA. Q4:B registers as statistically different than Q4:1046 with Student's t at P<0.05 for 28, 31, and 34 dpa.

Surprisingly, both BC lines matured significantly earlier than would be expected, given the recurrent parent (FIG. 7). The line carrying the high Brix associated allele at the QTL on linkage group 4 (Q4:B) matured at 33-34 DPA. This line is climacteric, and as such provides a simple and reliable indicator of physiological maturity, since it abscises from the vine ("slips"), at the time point when fruit quality and texture reach their optimum. The sister line (Q4:1046) by contrast slipped at 37 DPA, a full four days later than the near isogenic comparison Q4:B. The slipping point is indicated on FIG. 7 by an arrow. However, as noted, both mature earlier than the recurrent parent, indicating additional genes for earliness are harbored in the background. Additionally, the recurrent parent itself had poor fruit set in this trial, and could not therefore be evaluated past 37 DPA.

Q4:B accumulates Brix early (FIG. 7), reaching levels statistically indistinguishable from the final levels earlier than 28 DPA. In contrast, Q4:1046 is still increasing in Brix at each time point in this study and does not reach acceptable levels until 37 DPA. Data points in FIG. 7 represent LS Means of all samples measured for each line at each point. Table 10 enumerates numbers of fruit per data point.

TABLE 10

Sample count for Brix measurements represented in FIG. 7; DPA = days post anthesis; Count = number of melons assayed.

| Genotype | DPA | Count |
|---|---|---|
| Best | 28 | 20 |
|  | 31 | 20 |
|  | 34 | 19 |
|  | 37 | 20 |
| Q4:1046 | 28 | 20 |
|  | 31 | 20 |
|  | 34 | 18 |
|  | 37 | 20 |
| Q4:B | 28 | 20 |
|  | 31 | 19 |
|  | 34 | 19 |
| WSH1046 | 28 | 9 |
|  | 31 | 4 |
|  | 34 | 8 |
|  | 37 | 5 |

Collection of data found in FIG. 7 was performed as follows: on each harvest date, fruit were collected and for analysis on the day of harvest. Each fruit was weighed and then cut to remove a one inch thick planar sample half way between the blossom and stem end of the fruit. From the equatorial section, color was assessed using the Konica Minolta colorimeter CR400. The equatorial section was then carefully peeled and homogenized, filtered, and Brix determined using a benchtop refractometer. This protocol differs from field based Brix tests discussed elsewhere in the application in that the field method relies on sampling tissue at two points along the equatorial plane with a melon baller positioned mid way between the rind and the seed cavity. Although the field and laboratory methods consistently show the same relationships and trends, the lab based method includes more flesh from near the rind, and thereby results in lower Brix values by one half to one unit Brix, since melons have a rind to cavity gradient in sugar accumulation.

Example 7

Effect on Fruit Flesh Color

In addition to determining that the QTL on linkage group 4 confers earlier physiological maturity and Brix accumulation, the color of each fruit, and timing of coloration change, was measured, as this is another hallmark of fruit quality which occurs late in the maturation process. Q4:B develops approximately mature orange flesh color around 28 DPA. The increase in orange color intensity from 28 days to 34 days in the Q4:B line is 2.3 using the ΔE (CIE94) color difference formula (International Commission on Illumination ("CIE"); Vienna, Austria), which is designed to compare relative color differences. This difference is just above the minimum difference that can be detected by the human eye in a side by side comparison, and is not likely to be perceptibly different from expected mature flesh color in a non side-by-side comparison. In contrast, a color difference of 6.1 was observed for Q4:1046, showing that the magnitude of change in color over the last six days of maturation in this line is roughly three times more observable than that of the sister line. Further, Q4:B fruits have a deeper orange color at slip, thus the color of Q4:B at 28 DPA is predicted to be more ripe in appearance than Q4:1046 at 37 DPA. Importantly, it is known from consumer studies conducted in melons that consumers associate more vivid color with greater degrees of ripeness. It is especially surprising that the Q4:B line would exhibit a deeper orange color at maturity, given that the trait source 'Best' is a white-fleshed melon, however this appears to be a desirable linkage of the association of deeper color with early-maturing fruit. This study also confirmed the relationship between QTL4 and fruit size (also see Example 4 above), whereby fruit harboring Q4:B are smaller. However Q4:B fruit attain maximum size early in development as well, with no significant increases in size after 28 DPA. In contrast, Q4:1046 continues to expand up to slip.

Example 8

Fine Mapping of Brix QTL on LG10

Trials to fine map the Brix QTL on LG10 were conducted in Yuma, Ariz. (June 2011), Woodland, Calif. (August 2011) and Honduras (March 2012). In each trial, Brix was measured in $BC_2$-derived lines carrying recombination events at the targeted genomic region at the fruit harvest maturity. Data was analyzed in JMP (SAS Software, Cary, N.C., USA) using the appropriate mixed model to calculate Least Square Means (LSM) of 13 to 15 reps, depending on the experimental design of each trial, and Least Significant Differences (LSD) using the student's t-test.

In Yuma, trial entries suggested that the QTL is located within the interval of the markers NU0220114 and NU0220323 (1.67-4.48 cM), as entries Y11, Y7 and Y9 showed significantly higher Brix than entries Y12 and Y8 (Table 11A). However, there were no statistically significant differences between the control lines (which carried the donor introgression at the entire QTL interval) and the control lines carrying the recurrent parent introgression. Also, three entries (not shown) were discarded in this trial due to low germination that resulted in insufficient data points for analysis.

Data from the trial in Woodland demonstrated a trend in agreement with the data from the trial in Yuma. Entries W14, W10, W9 and W8 have higher Brix values than entries W6, W15, W13, W11 and W7 (Table 11B) which implies that the QTL is located in the interval of NU0219125 to NU0220323 (2.46-4.48 cM). Brix estimates for control entries in this trial (entries W1-W4) were also not significantly different from each other, but support that entries with donor introgressions at the QTL interval had higher Brix. Two entries were removed from this trial (not shown) due to their much larger fruit size, which has an impact on the Brix of the phenotyped fruits.

The trial conducted in Honduras (Table 11C) gave further evidence that the QTL is within the interval of the markers NU0220114 and NU0220323 (1.67-4.48 cM), as lines with the donor introgression at this region, as entries H7, H2, H5 and H3 showed significantly higher Brix than those with recurrent parent introgressions (entries H1, H6, and H4). Taken together, these three trials demonstrate that the QTL interval on LG10 between markers NU0220114 and NU0220323, between 1.67-4.48 cM, is of particular interest.

invention. More specifically, it will be apparent that certain agents that are both chemically and physiologically related may be substituted for the agents described herein while the same or similar results would be achieved. All such similar substitutes and modifications apparent to those skilled in the

TABLE 11

Fine mapping trials of Brix QTL on LG10 in (A) Yuma, AZ, (B) Woodland, CA and (C) Honduras. Least square means (LSM) and Least square differences (LSD) of Brix measured from BC$_2$-derived lines with recombination events within the QTL interval. RP: recurrent parent.

| | 1.67 NU0220114 | 2.46 NU0219125 | 4.48 NU0220323 | 5.74 NU0244737 | 7.53 NU0218664 | 12.61 NU0219683 | 14.33 NU0219142 | 18.82 NU0218502 | Entry | LSM | LSD |
|---|---|---|---|---|---|---|---|---|---|---|---|
| A | CC | CC | GG | AA | TT | TT | TT | GG | Y1 | 9.98 | C |
| | CC | CC | GG | AA | TT | TT | TT | GG | Y3 | 9.87 | C |
| | AA | TT | TT | GG | AA | CC | AA | AA | Y2 | 9.67 | C |
| | AA | TT | TT | GG | AA | CC | AA | AA | Y4 | 9.65 | C |
| | CC | TT | TT | GG | AA | CC | AA | AA | Y11 | 10.83 | B |
| | CC | CC | GG | AA | TT | CC | AA | AA | Y7 | 11.17 | AB |
| | CC | CC | GG | AA | TT | TT | AA | AA | Y9 | 11.77 | A |
| | AA | TT | GG | AA | TT | TT | TT | GG | Y12 | 9.41 | C |
| | AA | TT | TT | GG | AA | CC | TT | GG | Y8 | 9.90 | C |
| B | CC | CC | GG | AA | TT | TT | TT | GG | W1 | 9.75 | BC |
| | CC | CC | GG | AA | TT | TT | TT | GG | W3 | 10.79 | AB |
| | AA | TT | TT | GG | AA | CC | AA | AA | W2 | 8.76 | C |
| | AA | TT | TT | GG | AA | CC | AA | AA | W4 | 9.34 | BC |
| | AA | TT | TT | GG | AA | TT | TT | GG | W14 | 8.93 | C |
| | AA | TT | TT | GG | TT | TT | TT | GG | W10 | 8.99 | C |
| | AA | TT | TT | AA | TT | TT | TT | GG | W9 | 9.15 | C |
| | AA | TT | GG | AA | TT | TT | TT | GG | W8 | 9.06 | C |
| | AA | CC | GG | AA | TT | TT | TT | GG | W6 | 10.87 | AB |
| | CC | CT | TT | GG | AA | CC | AA | AA | W15 | 9.79 | BC |
| | CC | CC | GG | AA | AA | CC | AA | AA | W13 | 9.39 | BC |
| | CC | CC | GG | AA | TT | CC | AA | AA | W11 | 9.43 | BC |
| | CC | CC | GG | AA | TT | TT | AA | AA | W7 | 10.25 | ABC |
| C | CC | CC | TT | GG | AA | CC | AA | AA | H7 | 10.884 | A |
| | CC | TT | GG | AA | AA | CC | AA | AA | H2 | 8.747 | B |
| | CC | TT | GG | AA | TT | TT | TT | GG | H5 | 8.746 | B |
| | CC | TT | TT | GG | AA | CC | AA | AA | H3 | 8.556 | B |
| | AA | CC | GG | AA | TT | TT | TT | GG | H1 | 7.765 | C |
| | AA | CC | TT | AA | TT | TT | TT | GG | H6 | 7.739 | CD |
| | AA | CC | TT | GG | AA | TT | TT | GG | H4 | 7.124 | D |

▒ Donor Alleles
☐ RP Alleles

DEPOSIT INFORMATION

A deposit of melon line BEST, which is disclosed herein above and referenced in the claims, was made with the American Type Culture Collection (ATCC), 10801 University Blvd., Manassas, Va. 20110-2209. The date of deposit was Nov. 18, 2011 and the accession number for those deposited seeds of melon line BEST is ATCC Accession No. PTA-12263. All restrictions upon the deposit have been removed, and the deposit is intended to meet all of the requirements of 37 C.F.R. §1.801-1.809. The deposit will be maintained in the depository for a period of 30 years, or 5 years after the last request, or for the effective life of the patent, whichever is longer, and will be replaced if necessary during that period.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain art are deemed to be within the spirit, scope and concept of the invention as defined by the appended claims.

REFERENCES

The following references, to the extent that they provide exemplary procedural or other details supplementary to those set forth herein, are specifically incorporated herein by reference:

U.S. Pat. No. 5,463,175
U.S. Pat. No. 5,500,365
U.S. Pat. No. 5,633,435
U.S. Pat. No. 5,689,052
U.S. Pat. No. 5,880,275
Bernacchi et al., *Theor. Appl. Genet.*, 97:381-397, 1998.
Bird et al., *Biotech. Gen. Engin. Rev.*, 9:207, 1991.
EP 534 858
Gibson and Shillito, *Mol. Biotech.*, 7:125, 1997
Tanksley and Nelson, *Theor. Appl. Genet.*, 92:191-203, 1996
Wang et al., *Science*, 280:1077-1082, 1998.
Wang S., et al. Windows QTL Cartographer, Dept. of Statistics, N. Carolina State Univ., Raleigh, N.C. (www.statgen.ncsu.edu/qtlcart/WQTLCart.htm), 2011.
Williams et al., *Nucleic Acids Res.*, 1 8:6531-6535, 1990.
WO 99/31248

What is claimed is:

1. A cultivated *Cucumis melo* plant comprising at least a first introgressed chromosomal region conferring increased Brix content relative to a plant lacking the region, wherein the region is selected from the group consisting of a Brix content contributing QTL defined by flanking markers NU0219671 (SEQ ID NO: 1) and NU0218915 (SEQ ID NO: 74) on *Cucumis melo* linkage group 4, a Brix content contributing QTL defined by flanking markers NU0220114 (SEQ ID NO: 75) and NU0219142 (SEQ ID NO: 109) on *Cucumis melo* linkage group 10, and a Brix content contributing QTL defined by flanking markers NU0220114 (SEQ ID NO: 75) and NU0220323 (SEQ ID NO: 83) on *Cucumis melo* linkage group 10, wherein the Brix content contributing QTL is found in melon line BEST, and wherein a sample of seed of melon line BEST have been deposited under ATCC Accession Number PTA-12263.

2. The cultivated *Cucumis melo* plant of claim 1, wherein the plant comprises said Brix content contributing QTL defined by flanking markers NU0219671 (SEQ ID NO: 1) and NU0218915 (SEQ ID NO: 74) and said Brix content contributing QTL defined by flanking markers NU0220114 (SEQ ID NO: 75) and NU0219142 (SEQ ID NO: 109).

3. The cultivated *Cucumis melo* plant of claim 1, wherein the plant comprises said Brix content contributing QTL defined by flanking markers NU0220114 (SEQ ID NO: 75) and NU0219142 (SEQ ID NO: 109) and said Brix content contributing QTL defined by flanking markers NU0220114 (SEQ ID NO: 75) and NU0220323 (SEQ ID NO: 83).

4. The cultivated *Cucumis melo* plant of claim 1, wherein the plant comprises said Brix content contributing QTL defined by flanking markers NU0219671 (SEQ ID NO: 1) and NU0218915 (SEQ ID NO: 74) and said Brix content contributing QTL defined by flanking markers NU0220114 (SEQ ID NO: 75) and NU0220323 (SEQ ID NO: 83).

5. The *Cucumis melo* plant of claim 1, further defined as one of the market class group consisting of Piel de Sapo, Juan Canary, Amarillo, Earl's Type, Honeydew, Orange-flesh honeydew, Hami Melon, Crenshaw, Casaba, Ananas, Galia, Charentais, Italian-type, and Western Shipper.

6. The *Cucumis melo* plant of claim 1, wherein the plant is homozygous for said chromosomal region.

7. The *Cucumis melo* plant of claim 1, wherein the plant produces fruit with an average Brix content of at least 9° Brix at fruit maturity.

8. The *Cucumis melo* plant of claim 1, wherein the chromosomal region confers an increase of at least 1° Brix relative to an otherwise essentially isogenic plant lacking the chromosomal region.

9. The plant of claim 1, wherein the plant is inbred.

10. The plant of claim 1, wherein the plant is hybrid.

11. A seed of the plant of claim 1, wherein said seed comprises said Brix content contributing QTL found in melon line BEST, and wherein a sample of seed of melon line BEST has been deposited under ATCC Accession Number PTA-12263.

12. A plant part of the plant of claim 1, wherein said plant part comprises said Brix content contributing QTL found in melon line BEST, and wherein a sample of seed of melon line BEST has been deposited under ATCC Accession Number PTA-12263.

13. The plant part of claim 12, wherein the plant part is selected from the group consisting of a leaf, pollen, an ovule, a fruit, rootstock, a scion, and a cell.

14. The plant part of claim 13, wherein the plant part is a fruit.

15. A tissue culture of regenerable cells of the plant of claim 1.

16. A tissue culture according to claim 15, comprising cells or protoplasts from a plant part selected from the group consisting of an embryo, a meristem, a cotyledon, pollen, a leaf, anthers, a root, a root tip, pistil, flower, seed and a stalk.

17. The cultivated *Cucumis melo* plant of claim 1, wherein the plant comprises said Brix content contributing QTL defined by flanking markers NU0219671 (SEQ ID NO: 1) and NU0218915 (SEQ ID NO: 74) and said Brix content contributing QTL defined by flanking markers NU0220114 (SEQ ID NO: 75) and NU0220323 (SEQ ID NO: 83) and said Brix content contributing QTL defined by flanking markers NU0220114 (SEQ ID NO: 75) and NU0219142 (SEQ ID NO: 109).

* * * * *